United States Patent [19]

Effland et al.

[11] Patent Number: 5,032,599

[45] Date of Patent: * Jul. 16, 1991

[54] N-(PYRROL-L-YL)PYRIDINAMINES

[75] Inventors: Richard C. Effland; Joseph T. Klein; Kevin J. Kapples, all of Bridgewater, N.J.

[73] Assignee: Hoechst-Roussel Pharmaceuticals Inc., Somerville, N.J.

[*] Notice: The portion of the term of this patent subsequent to Jun. 2, 2005 has been disclaimed.

[21] Appl. No.: 245,252

[22] Filed: Sep. 16, 1988

Related U.S. Application Data

[60] Division of Ser. No. 926,593, Nov. 12, 1986, Pat. No. 4,792,562, which is a continuation-in-part of Ser. No. 804,430, Dec. 4, 1985, Pat. No. 4,752,610.

[51] Int. Cl.$^5$ .................. A61K 31/44; A61K 31/445; C07D 401/02
[52] U.S. Cl. .................... 514/343; 514/318; 514/333; 546/193; 546/256; 546/281
[58] Field of Search ....................... 546/281, 193, 256; 514/343, 333, 318

[56] References Cited

U.S. PATENT DOCUMENTS

| 4,631,286 | 12/1986 | Shutske et al. | 514/297 |
| 4,670,562 | 6/1987 | Martin et al. | 546/94 |
| 4,695,573 | 9/1987 | Shutske et al. | 514/290 |

Primary Examiner—Alan L. Rotman
Attorney, Agent, or Firm—Tatsuya Ikeda

[57] ABSTRACT

There are disclosed novel compounds of the formula

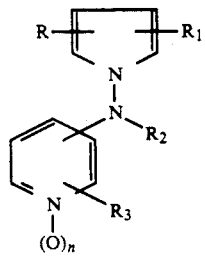

where n is 0 or 1; R is hydrogen or loweralkyl; $R_1$ is hydrogen, loweralkyl, halogen, cyano, loweralkanoyl, arylloweralkanoyl, aroyl, —CH(OH)$R_4$, —C-(OH)$R_4R_5$ or —CH$_2$OR$_5$, —CH=CR$_6R_7$, —CH=CHCN, —CH=CHOCH$_3$, —CH=CH-CO$_2$C$_2$H$_5$,

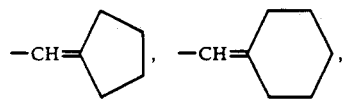

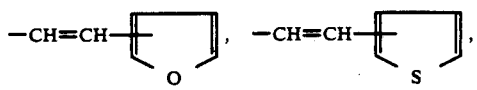

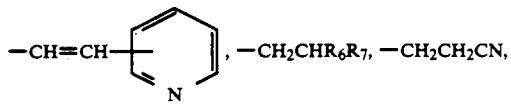

—CH$_2$CH$_2$OCH$_3$, —CH$_2$CH$_2$CO$_2$C$_2$H$_5$,

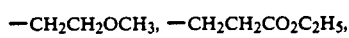

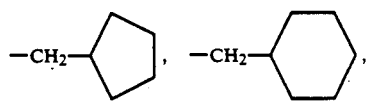

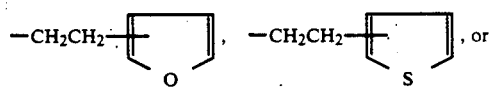

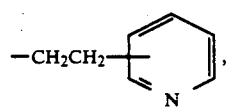

$R_4$ being hydrogen, loweralkyl, arylloweralkyl or aryl, $R_5$ being loweralkyl, aryl or arylloweralkyl, $R_6$ being hydrogen or loweralkyl and $R_7$ being hydrogen, loweralkyl or aryl; $R_2$ is hydrogen, loweralkyl, loweralkenyl, loweralkynyl, —CH$_2$CO$_2$C$_2$H$_5$, arylloweralkyl, phenyl, nitrophenyl, cyanophenyl, trifluoromethylphenyl, aminophenyl, loweralkanoylaminophenyl, loweralkoxycarbonyl, arylloweralkoxycarbonyl, aryloxycarbonyl, loweralkylaminocarbonyl, arylloweralkylaminocarbonyl, arylaminocarbonyl, alkanoyl, arylloweralkanoyl, aroyl, alkenoyl, alkynoyl, —CH$_2$C≡CCH$_2$—NR'R'', —CH$_2$CH=CHCH$_2$—NR'R'' or —CH$_2$CH$_2$CH$_2$CH$_2$—NR'R'', R' and R'' being independently loweralkyl or —NR'R'' taken as a whole being

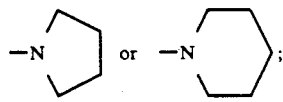

and $R_3$ is hydrogen, NO$_2$, NH$_2$, halogen, loweralkanoylamino, arylloweralkanoylamino, aroylamino or loweralkyl; with the proviso that when n is 0, $R_2$ is phenyl, $R_3$ is hydrogen and the pyridine moiety is 2-pyridinyl, R and $R_1$ may not be 2-methyl and 5-methyl; or pharmaceutically acceptable acid addition salts thereof, which are useful for enhancing memory, methods for synthesizing them, pharmaceutical compositions comprising an effective memory enhancing amount of such a compound and a method of treating a patient in need of memory enhancement which comprises administering such a compound to the patient.

45 Claims, No Drawings

N-(PYRROL-L-YL)PYRIDINAMINES

This is a division of a prior application Ser. No. 926,593, filed Nov. 12, 1986, now U.S. Pat. No. 4,792,562, which in turn is a continuation-in-part of a prior application Ser. No. 804,430 filed Dec. 4, 1985, now U.S. Pat. No. 4,752,610.

This invention relates to novel compounds of the formula

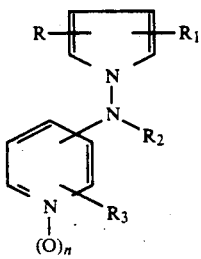

(I)

where n is 0 or 1; R is hydrogen or loweralkyl; $R_1$ is hydrogen, loweralkyl, halogen, cyano, loweralkanoyl, arylloweralkanoyl, aroyl, —CH(OH)$R_4$, —C(OH)$R_4R_5$ or —CH$_2$OR$_5$, —CH=CR$_6$R$_7$, —CH=CHCN, —CH=CHOCH$_3$, —CH=CH-CO$_2$C$_2$H$_5$,

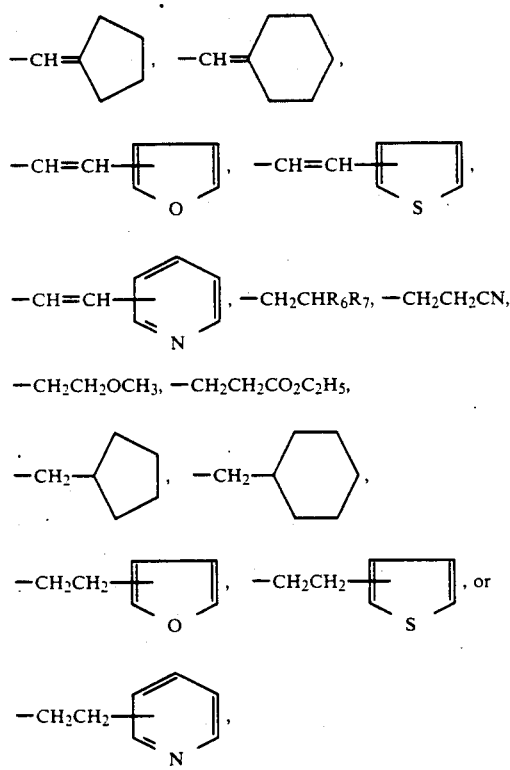

$R_4$ being hydrogen, loweralkyl, arylloweralkyl or aryl, $R_5$ being loweralkyl, aryl or arylloweralkyl, $R_6$ being hydrogen or loweralkyl and $R_7$ being hydrogen, loweralkyl or aryl; $R_2$ is hydrogen, loweralkyl, loweralkenyl, loweralkynyl, —CH$_2$CO$_2$C$_2$H$_5$, arylloweralkyl, phenyl, nitrophenyl, cyanophenyl, trifluoromethylphenyl, aminophenyl, loweralkanoylaminophenyl, loweralkoxycarbonyl, arylloweralkoxycarbonyl, aryloxycarbonyl, loweralkylaminocarbonyl, arylloweralkylaminocarbonyl, arylaminocarbonyl, alkanoyl, arylloweralkanoyl, aroyl, alkenoyl, alkynoyl, —CH$_2$C≡CCH$_2$—NR'R", —CH$_2$CH=CHCH$_2$—NR'R" or —CH$_2$CH$_2$CH$_2$CH$_2$—NR'R", R' and R" being independently loweralkyl or —NR'R" taken as a whole being

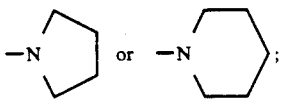

and $R_3$ is hydrogen, NO$_2$, NH$_2$, halogen, loweralkanoylamino, arylloweralkanoylamino, aroylamino or loweralkyl; with the proviso that when n is 0, $R_2$ is phenyl, $R_3$ is hydrogen and the pyridine moiety is 2-pyridinyl, R and $R_1$ may not be 2-methyl and 5-methyl; or pharmaceutically acceptable acid addition salts thereof, which are useful for enhancing memory, methods for synthesizing them, pharmaceutical compositions comprising an effective memory enhancing amount of such a compound and a method of treating a patient in need of memory enhancement which comprises administering such a compound to the patient.

Throughout the specification and the appended claims, a given chemical formula or name shall encompass all stereo, optical, and geometrical isomers thereof where such isomers exist, as well as pharmaceutically acceptable acid addition salts thereof and solvates thereof such as for instance hydrates.

The following general rules of terminology shall apply throughout the specification and the appended claims.

Unless otherwise stated or indicated, the term loweralkyl denotes a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

Unless otherwise stated or indicated, the term loweralkoxy denotes a straight or branched alkoxy group having from 1 to 6 carbon atoms. Examples of said loweralkoxy include methoxy, ethoxy, n-propoxy, iso-propoxy, n-butoxy, iso-butoxy, sec-butoxy, t-butoxy and straight- and branched-chain pentoxy and hexoxy.

Unless otherwise stated or indicated, the term halogen shall mean fluorine, chlorine, bromine or iodine.

Unless otherwise stated or indicated, the term aryl shall mean a phenyl group having 0, 1, 2 or 3 substituents each of which being independently loweralkyl, loweralkoxy, halogen, CF$_3$, NO$_2$ or CN. Unless otherwise stated or indicated, the term alkyl shall mean a saturated hydrocarbon group of 1 to 20 carbon atoms, the term alkenyl shall mean a hydrocarbon group of 1-20 carbon atoms having one or more carbon-carbon double bonds, and the term alkynyl shall mean a hydrocarbon group of 1-20 carbon atoms having one or more carbon-carbon triple bonds.

The term loweralkanoic acid shall mean a carboxylic acid in which the carboxyl group is attached to hydrogen or an alkyl group of from 1 to 5 carbon atoms.

The term loweralkanoyl shall mean a group obtained by removing a hydroxy group from the carboxyl group of a loweralkanoic acid, and thus it includes for instance formyl, acetyl and the like.

The term arylloweralkanoyl shall mean a loweralkanoyl group having an aryl substituent thereon, the terms loweralkanoyl and aryl having the respective meanings defined above.

The term aroyl shall mean arylcarbonyl, an example being benzoyl.

The term arylloweralkyl shall mean a loweralkyl group having an aryl substituted thereon, the terms loweralkyl and aryl having the respective meanings defined above.

The terms alkanoyl, alkenoyl and alkynoyl shall mean groups obtained by removing a hydroxy group from the carboxyl group of alkanoic acid, alkenoic acid and alkynoic acid, respectively. Thus, for instance, linoleyl group derived from linoleic acid is an example of the term alkenoyl as defined above.

The term acyl shall mean loweralkanoyl or arylloweralkanoyl as defined above.

The compounds of formula (I) of this invention can be synthesized by following or combining one or more of the steps described below, not necessarily in the order presented. Throughout the description of the synthetic steps, the definitions of R, $R_1$ through $R_7$, R' and R" and n are as given above unless otherwise stated or indicated, and other nomenclatures appearing below shall have the same meanings defined in their respective first appearances unless otherwise stated or indicated.

STEP A

A compound of formula (II) where $R_8$ is H, loweralkyl, halogen or cyano and $R_9$ is H, loweralkyl or phenyl is reacted with a compound of formula (III) where X is chlorine or fluorine and $R_{10}$ is H, $NO_2$, halogen or loweralkyl to afford a compound of formula (IV).

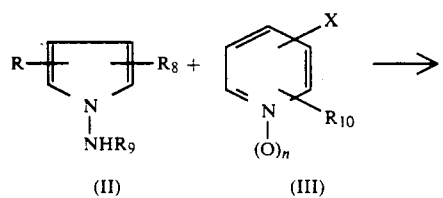

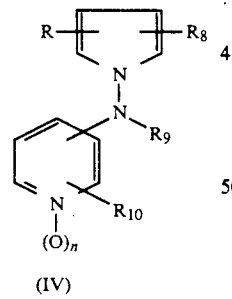

Said reaction is typically conducted in an ethereal solvent such as bis(2-methoxyethyl)ether, diethyl ether, dimethoxy ether, dioxane or tetrahydrofuran or polar aprotic solvent such as dimethylformamide, dimethylacetamide, hexamethylphosphoramide or dimethylsulfoxide at a temperature of between about 20° C. and 150° C.

STEP B

As an alternative to STEP A, when $R_8$ is H or loweralkyl, compound IV can be obtained by reacting a compound of formula (V) with a compound of formula (VI).

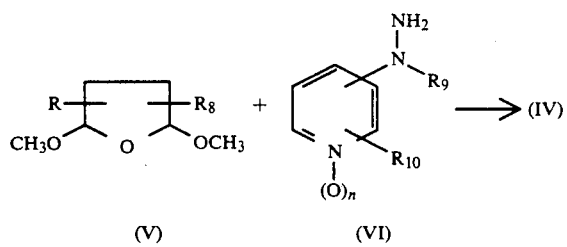

Said reaction is typically conducted in an alkanoic acid, preferably loweralkanoic acid such as glacial acetic acid, propanoic acid or formic acid at a temperature of about 80°–120° C.

STEP C

A compound of formula IVa is treated with a strong base such as sodium hydride or potassium hydride in a suitable solvent such as polar aprotic solvent including dimethylformamide, dimethylsulfoxide and ethereal solvents or aromatic hydrocarbon at a temperature of between about −10° and 50°, preferably 0°–25° to form the anion of IVa, which is reacted with a loweralkyl or arylloweralkyl halide of formula $R_{11}$—X, where $R_{11}$ is loweralkyl, $-CH_2CO_2C_2H_5$, loweralkenyl, loweralkynyl or arylloweralkyl and X is Cl, Br or I at a temperature of between about −10° and 80°, preferably between 0° and 25°

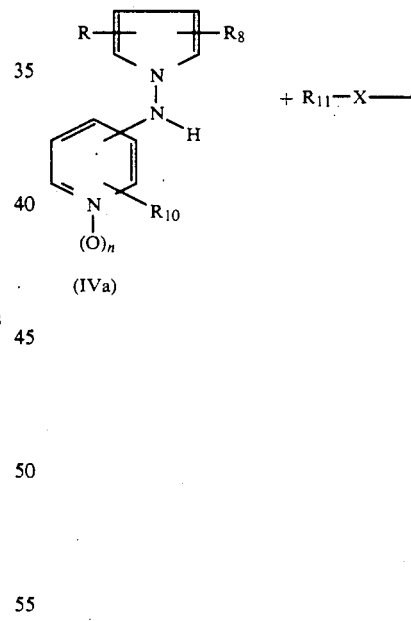

STEP D

The anion of IVa, prepared as in STEP C, is reacted with fluoro-nitrobenzene, cyano-fluorobenzene or fluoro-trifluoro-methylbenzene of formula

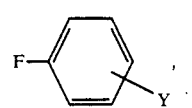

where Y is nitro, cyano or trifluoromethyl to afford a compound of formula (VIII) below.

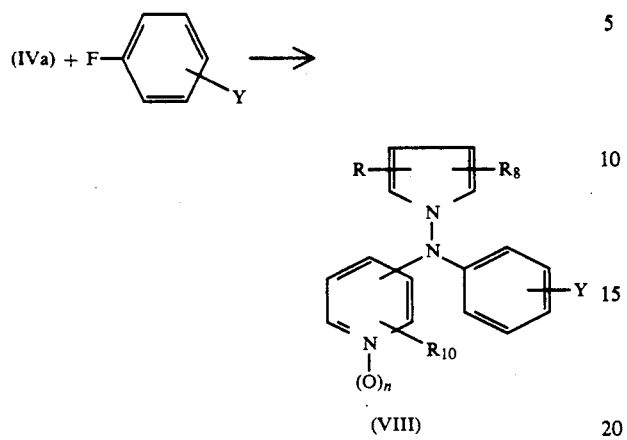

Said reaction is conducted in substantially the same manner as in STEP C.

STEP E

Compound IVa is reacted with a loweralkyl isocyanate, arylloweralkyl isocyanate or aryl isocyanate of formula $R_{12}NCO$ where $R_{12}$ is loweralkyl, arylloweralkyl or aryl to afford a compound of formula (IX).

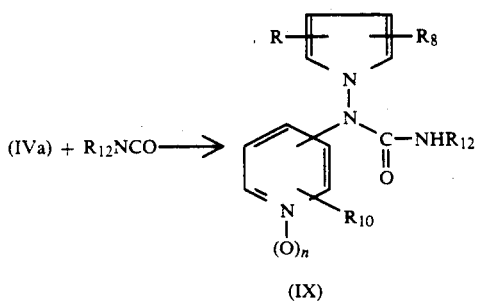

Said reaction is typically conducted in a suitable solvent such as aromatic hydrocarbon including benzene, toluene and the like, halogenated hydrocarbon or ethereal solvent at a temperature of about 0°–80°, preferably 30°–60° C.

STEP F

Compound IVa is reacted with a loweralkyl chloroformate, arylloweralkyl chloroformate or aryl chloroformate of formula $Cl\text{-}CO\text{-}OR_{12}$ to afford a compound of formula (X).

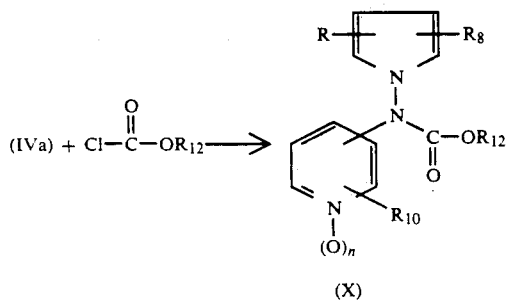

Said reaction is conducted under substantially the same conditions as used in STEP E.

STEP G

Compound IVa is reacted with an alkanoyl chloride, arylloweralkanoyl chloride, aroyl chloride, alkenoyl chloride or alkynoyl chloride of formula (XI) where $R_{13}$ is alkyl, arylloweralkyl, aryl, alkenyl or alkynyl to afford a compound of formula (XII).

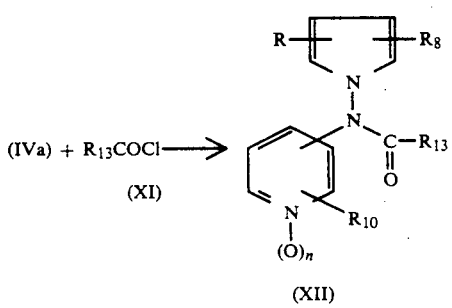

Said reaction is typically conducted under substantially the same conditions as used in STEP E or F.

Where the compound $R_{13}COCl$ is not commercially available, it is prepared from the corresponding carboxylic acid $R_{13}COOH$ and thionyl chloride in a suitable solvent, for instance, in benzene at the reflux temperature.

STEP H

As an alternative to STEP A, B or C, a compound of formula (IVb) where $R_{14}$ is loweralkyl can be prepared by reacting compound IVa with a strong base such as sodium hydride or potassium hydride and then reacting the product with a diloweralkyl sulfate of the formula $(R_{14})_2SO_4$.

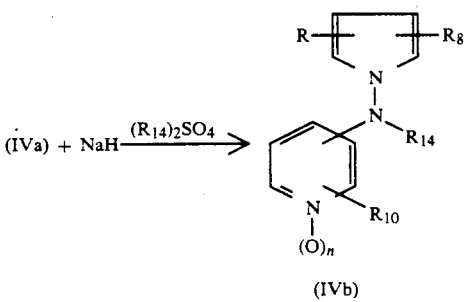

Said two steps are conducted under substantially the same conditions as used in STEP C.

STEP I

A compound of formula VIIa obtained in STEP C is subjected to Mannich reaction with formaldehyde and a secondary amine of the formula HNR'R", where R' and R" are as defined earlier to afford a compound of formula XIII.

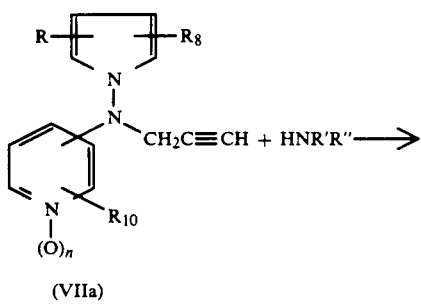

(VIIa)

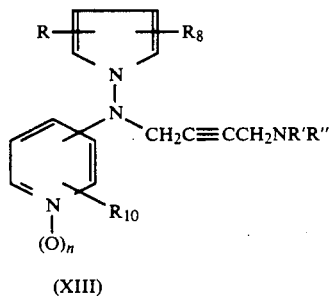

(XIII)

The above reaction can be conducted under conditions usually used in the art for carrying out Mannich reactions. Typically, it is conducted by preparing a mixture of compound VIIa, paraformaldehyde, HNR'R", cuprous chloride (used as a catalyst) and a suitable medium including ethereal solvents such as dioxane, and heating the mixture at 25°–100°.

STEP J

Compound XIII is catalytically hydrogenated to afford a compound of formula XIV or XV by making a suitable selection of reaction conditions in a manner known to the art.

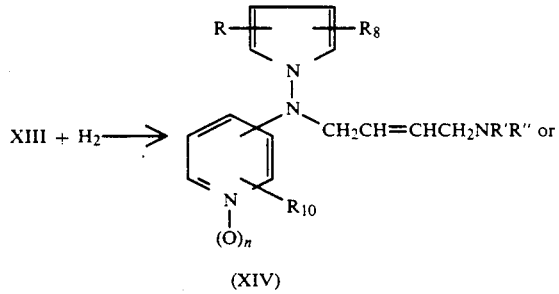

(XIV)

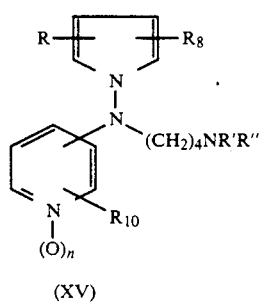

(XV)

STEP K

As an alternative to the foregoing steps, a compound of formula (XVI) where $R_{15}$ is loweralkyl, —CH$_2$CO$_2$C$_2$H$_5$, arylloweralkyl, aryl, loweralkoxycarbonyl, arylloweralkoxycarbonyl, aryloxycarbonyl, alkanoyl, arylloweralkanoyl or aroyl can be prepared by reacting a compound of formula (XVII) with N-chlorosuccinimide (NCS).

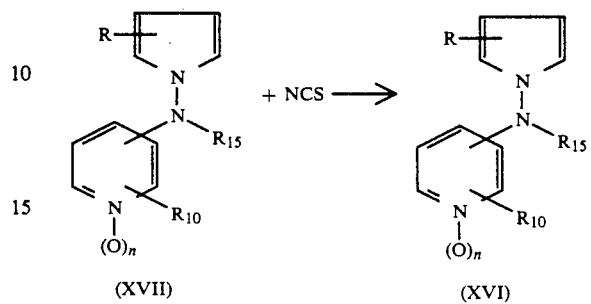

(XVII)  (XVI)

Said chlorination is conducted typically in a suitable solvent such as ethereal solvent or halogenated hydrocarbon at a temperature of about 0°–60° C.

STEP L

A compound of formula (XVIII) where $R_2$ is loweralkyl, loweralkoxycarbonyl, alkanoyl, alkenoyl, alkynoyl, arylloweralkanoyl or aroyl, and $R_{16}$ is H, NO$_2$, halogen or loweralkyl which is prepared by use of one or more of the reaction steps described in this specification is reacted with phosphorus oxychloride and dimethylformamide to afford a compound of formula (XIX).

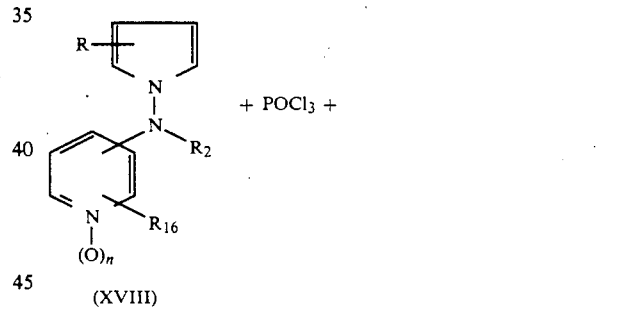

(XVIII)

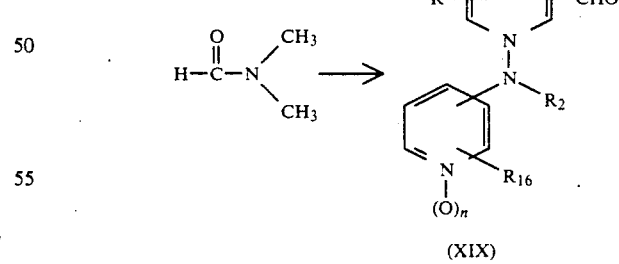

(XIX)

Said reaction can be conducted under conditions usually used for carrying out Vilsmeier reactions. Typically, it is conducted in a suitable solvent such as halogenated hydrocarbon at a temperature of about 20°–100° C.

STEP M

Compound XVIII is reacted with a loweralkanoyl chloride, arylloweralkanoyl chloride or aroyl chloride of formula $R_{12}COCl$ in the presence of zinc chloride to afford a compound of formula (XX).

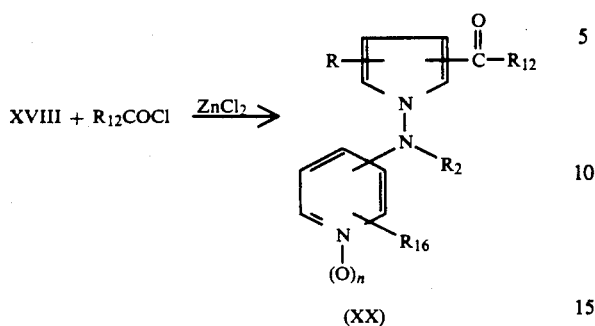

(XX)

Said reaction is typically conducted in a suitable solvent such as halogenated hydrocarbon at a temperature of about 20°–100° C.

STEP N

A compound of formula XXI below where $R_{17}$ is H, halogen or loweralkyl is reduced to a compound of formula XXII below with $NaBH_4$, $LiAlH_4$ or borane complexes.

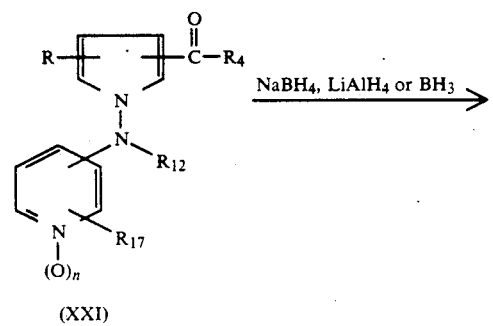

(XXI)

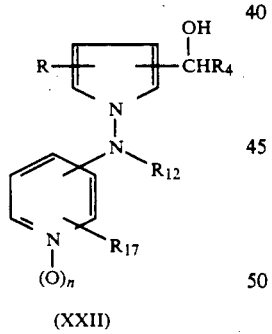

(XXII)

When $NaBH_4$ is used, said reduction is conducted typically in a lower aliphatic alcohol such as isopropanol or ethanol or loweralkanoic acid at a temperature of about 0°–80°. After the reaction, water is added to the reaction mixture. When $LiAlH_4$ is used, said reduction is conducted typically in an ethereal solvent such as tetrahydrofuran or ether at a temperature of about 0°–80°. When borane complexes are used, the reaction temperature is typically 0°–80° C.

STEP O

Compound XXI is reacted with a Grignard reagent of the formula $R_5MgBr$ (where $R_5$ is loweralkyl as defined earlier) and the product is thereafter hydrolyzed to afford a compound of formula (XXIII) below.

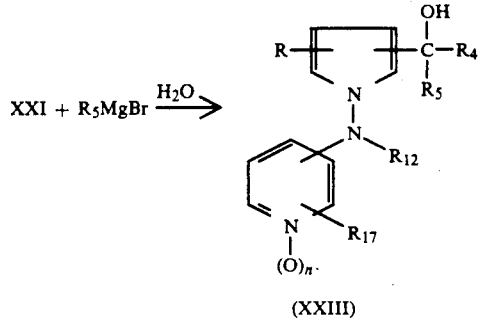

(XXIII)

STEP P

A compound of formula (XXIV) which is prepared by use of one or more of the reaction steps described in this specification is catalytically hydrogenated with hydrogen gas and a suitable catalyst such as palladium on carbon to afford a compound of formula (XXV).

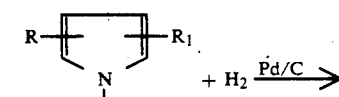

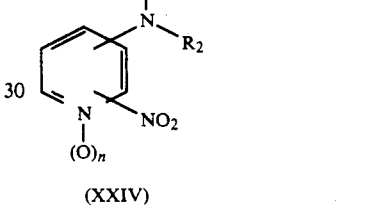

(XXIV)

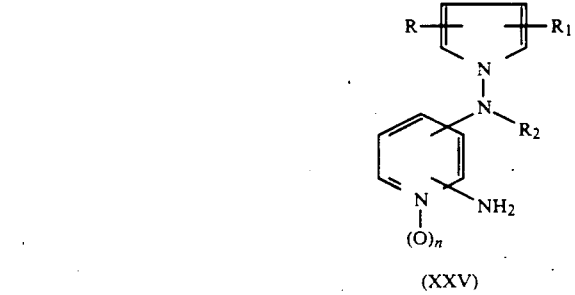

(XXV)

Said catalytic hydrogenation is typically conducted in a suitable solvent such as loweralkanol or loweralkyl ester of loweralkanoic acid at a temperature of 20°–50° C.

STEP Q

As an alternative to the foregoing steps, compound IVa can be prepared by hydrolyzing compound X. (Needless to say, the purpose of this STEP is not to reverse aforementioned STEP F in order to regain the starting compound of STEP F. This STEP can be useful, for instance, for the purpose of converting $R_8$ in formula IVa from hydrogen to 2-chloro. Thus, for this purpose, one can first convert the amino hydrogen in formula IVa to ethoxycarbonyl by use of STEP F and then introduce chlorine into the 2-position of the pyrrole ring by use of STEP K, and thereafter hydrolyze the resultant product by use of this STEP, instead of conducting the N-chlorosuccinimide reaction directly with compound IVa. Similarly, this STEP can also be useful for introducing the group $—COR_{12}$ into the pyrrole ring according to STEP M above or the group —CHO according to STEP L when $R_2$ is hydrogen.

$$(X) + H_2O \rightarrow (IVa)$$

Said hydrolysis is conducted typically by stirring a mixture comprising compound X, an alkali such as NaOH and a suitable medium such as ethanol plus water at a temperature of about 70°-100° C.

STEP R

Compound XXV is reacted with phenyl formate to afford a compound of formula (XXVI)

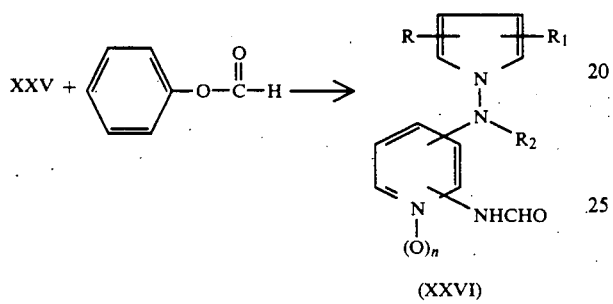

(XXVI)

Typically said reaction is conducted by stirring a solution of compound XXV in excess phenyl formate at a temperature of about 20°-50° C. The same reaction can also be conducted with loweralkyl formate under substantially the same conditions.

STEP S

Compound XXV is reacted with an acyl chloride of the formula $R_{12}COCl$ or acid anhydride of the formula $R_{12}CO-O-COR_{12}$ to afford a compound of formula XXVII.

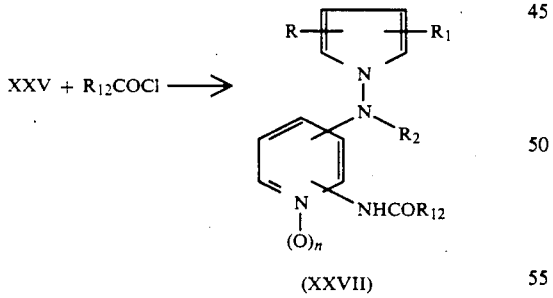

(XXVII)

Said reaction is conducted under substantially the same conditions as used in STEP G.

STEP T

As an alternative to the foregoing steps, a compound of formula (XXVIII) where $R_1$ is H or loweralkyl, and $R_2$ is loweralkyl, arylloweralkyl, phenyl, nitrophenyl, or trifluoromethylphenyl, can be prepared by reacting a compound of formula (IVc) with a loweralkyl lithium of the formula $R_{18}Li$ where $R_{18}$ is loweralkyl.

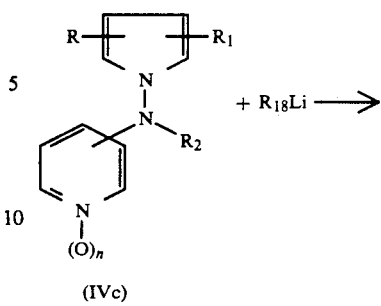

(IVc)

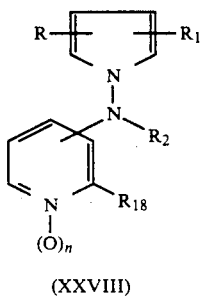

(XXVIII)

Said reaction is usually conducted in a suitable solvent such as ethereal solvent, preferably tetrahydrofuran at a temperature of between about $-10°$ C. and 50° C.

STEP U

A compound of formula (XXIIa) below is reacted with a strong base such as sodium hydride or potassium hybride and the resultant alkoxide anion is reacted with a halide of the formula $R_5X$ to afford an ether of formula (XXIX) below. Said two-step procedure is conducted in substantially the same manner as in STEP C above.

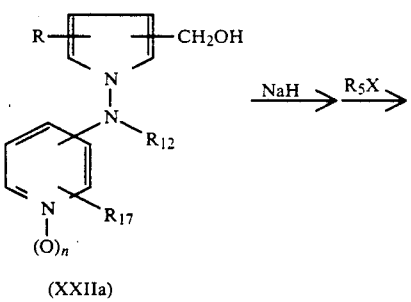

(XXIIa)

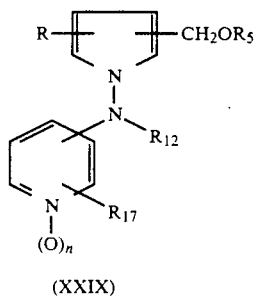

(XXIX)

STEP V

Compound XIX is subjected to Wittig reaction with an ylide of the formula $(C_6H_5)_3P=R_{19}$ to afford a compound of formula XXX where the group $=R_{19}$ is $=CR_6R_7$, $=CHCN$, $=CHOCH_3$, $=CHCO_2C_2H_5$,

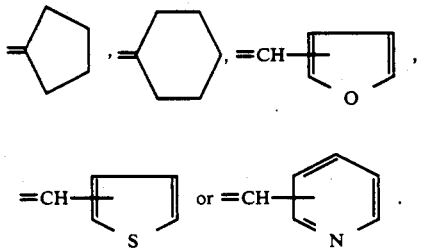

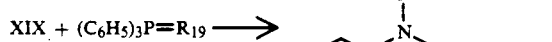

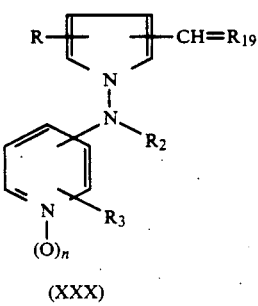

(XXX)

The above reaction can be conducted under conditions usually used for carrying out Wittig reactions. Thus, the ylide is prepared in a routine manner by first preparing a phosphonium salt from a bromide of the formula $Br-R_{19}-H$ and triphenylphosphine and thereafter reacting the phosphonium salt with a suitable base such as sodium hydride, potassium tert-butoxide or n-butyllithium in a suitable solvent such as anhydrous ethereal solvent. Thereafter a solution of compound XIX in a suitable solvent such as anhydrous ether is added to the freshly prepared ylide solution and the mixture is stirred at a temperature of between about $-10°$ C. and $80°$ C.

STEP W

Compound XXX is catalytically hydrogenated in a suitable manner known to the art to afford a compound of formula XXXI.

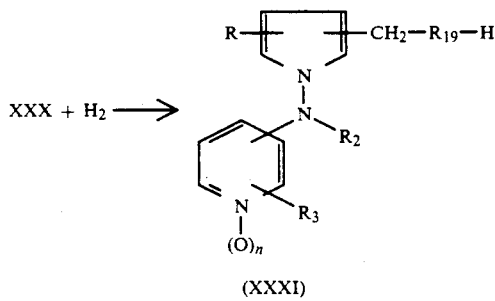

(XXXI)

STEP X

Substantially the same hydrogenation technique as described in STEP P or W can be used to hydrogenate a compound of formula XXXII below to afford a compound of formula XXXIII below.

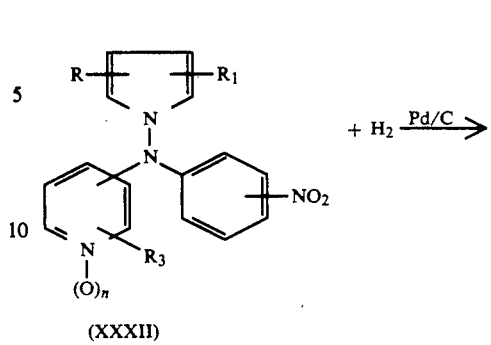

(XXXII)

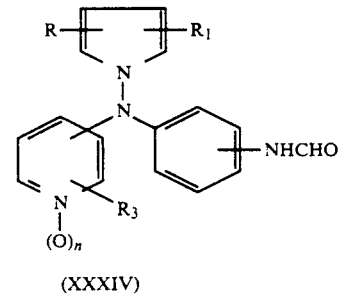

(XXXIII)

STEP Y

Substantially the same reaction technique as described in STEP R can be used to convert compound XXXIII to a compound of formula XXXIV below.

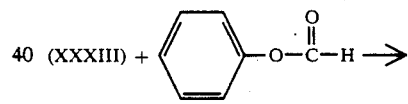

(XXXIII) +

[phenyl formate structure] →

[compound XXXIV structure with NHCHO group]

(XXXIV)

STEP Z

Substantially the same reaction technique as described in STEP S can be used to convert compound XXXIII to a compound of formula XXXV below.

(XXXIII) + $R_{12}COCl$ →

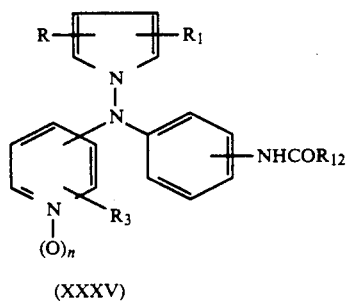

(XXXV)

STEP AA

As an alternative to the foregoing steps, introduction of a cyano group into the pyrrole ring can be accomplished by using, as a starting compound, the aforementioned formyl compound of formula XIX and converting the formyl group into a cyano group. For this purpose, compound XIX is first reacted with hydroxylamine in a routine manner to obtain the corresponding oxime and thereafter the oxime is reacted with benzenesulfonyl chloride to obtain a nitrile compound of formula XXXVI.

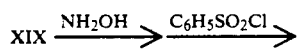

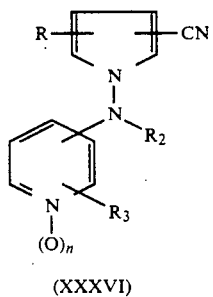

(XXXVI)

The second step is typically conducted in a suitable solvent such as ethereal solvent by warming the reaction mixture at 60°–100° C.

The N-(pyrrol-1-yl)pyridinamine compounds of formula I of the present invention are useful in the treatment of various memory dysfunctions characterized by decreased cholinergic function, such as Alzheimer's disease.

Cholinergic agonists have been shown to have increased affinity for [$^3$H]-QNB (quinuclidinyl benzilate) binding sites in the presence of zinc ions. Thus, enhanced [$^3$H]-QNB displacement by a compound in the presence of zinc is taken as a measure of cholinergic agonist activity, and would therefore be useful in the treatment of Alzheimer's disease.

[$^3$H]-QNB DISPLACEMENT ASSAY

The ability to displace [$^3$H]-QNB in the presence and absence of zinc ions was determined by the method of C. P. Smith and F. P. Huger, Biochemical Pharmacology, 32, 377 (1983).

| Compound | IC$_{50}$ W/O Zinc | IC$_{50}$ With Zinc | Ratio W/O Zinc/ With Zinc |
|---|---|---|---|
| N-(1H-Pyrrol-1-yl)-4-pyridinamine | $3.67 \times 10^{-4}$ | $3.04 \times 10^{-5}$ | 12.2 |
| N-Methyl-N-(1H-pyrrol-1-yl)-4-pyridinamine | $1.42 \times 10^{-4}$ | $1.32 \times 10^{-5}$ | 10.7 |
| 1-[N-Methyl-N-(4-pyridinyl)]-aminopyrrole-3-carboxaldehyde | $1.85 \times 10^{-4}$ | $3.29 \times 10^{-5}$ | 5.6 |
| N-[2-(1-hydroxyethyl)-1H-pyrrol-1-yl]-N-methyl-4-pyridinamine | $1.73 \times 10^{-4}$ | $2.2 \times 10^{-5}$ | 7.8 |
| N-(2-chloro-1H-pyrrol-1-yl)-N-ethyl-4-pyridinamine | $3.34 \times 10^{-5}$ | $5.4 \times 10^{-6}$ | 6.2 |
| Pilocarpine (reference compound) | $5.80 \times 10^{-6}$ | $1.72 \times 10^{-6}$ | 3.4 |

This utility is further demonstrated by the ability of these compounds to restore cholinergically deficient memory in the Dark Avoidance Assay, where they are in general active over a broader dose range than heretofore known compounds, a distinct therapeutic advantage.

Dark Avoidance Asssay

In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scolopamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment.

| Compound | Dose mg/kg by Body Weight | % of Animals With Scopolamine Induced Memory Deficit Reversed |
|---|---|---|
| N-(1H-Pyrrol-1-yl)-4-pyridinamine | 0.63 | 21 |
| N-Methyl-N-(1H-pyrrol-1-yl)-4-pyridinamine | 2.5 | 43 |
| 1-[N-Methyl-N-(4-pyridinyl)]amino-pyrrole-2-carboxaldehyde | 1.25 | 60 |
| N-[2-(1-hydroxyethyl)-1H-pyrrol-1-yl]-N-methyl-4-pyridinamine | 5.0 | 19 |

| Compound | Dose mg/kg by Body Weight | % of Animals With Scopolamine Induced Memory Deficit Reversed |
|---|---|---|
| N-(2-Chloro-1H-pyrrol-1-yl)-N-ethyl-4-pyridinamine | 2.5 | 33 |
| Pilocarpine (reference compound) | 5 | 23 |

Additionally, some of the compounds of this invention exhibit antidepressant activities, which activities being particularly helpful for patients suffering from Alzheimer's disease. Further, the compounds of this invention are in general less toxic than heretofore known compounds such as tacrine and physostigmine, making them more therapeutically acceptable.

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such composition is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatin; an excipient such as starch or lactose, a disintegrating agent such as alginic acid, Primogel, cornstarch and the like; a lubricant such as magnesium stearate or Sterotex; a glidant such as colloidal silicon dioxide; n a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied depending upon the particular form and may coveniently be between 4% and about 70% of the weight of the unit. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:
N-(1H-pyrrol-1-yl)-4-pyridinamine;
N-methyl-N-(1H-pyrrol-1-yl)-3-nitro-4-pyridinamine;
3-nitro-N-(1H-pyrrol-1-yl)-4-pyridinamine;
N-(4-pyridinyl)-N-(1H-pyrrol-1-yl)-N'-methylurea;
N-(4-pyridinyl)-N-(1H-pyrrol-1-yl)carbamic acid ethyl ester;
N-(4-pyridinyl)-N-(1H-pyrrol-1-yl)propanamide;
N-(4-pyridinyl)-N-(1H-pyrrol-1-yl)linoleamide;
N-(2-chloro-1H-pyrrol-1-yl)-N-(4-pyridinyl)-linoleamide;
N-(4-pyridinyl)-N-(1H-pyrrol-1-yl)-phenylacetamide;
3,4-dimethoxy-N-(4-pyridinyl)-N-(1H-pyrrol-1-yl)phenylacetamide;
N-(2-chloro-1H-pyrrol-1-yl)-N-(4-pyridinyl)-3,4-dimethoxyphenylacetamide;
N-methyl-N-(1H-pyrrol-1-yl)-4-pyridinamine;
N-ethyl-N-(1H-pyrrol-1-yl)-4-pyridinamine;
N-propyl-N-(1H-pyrrol-1-yl)-4-pyridinamine;
N-phenylmethyl-N-(1H-pyrrol-1-yl)-4-pyridinamine;
N-(butyl)-N-(1H-pyrrol-1-yl)-4-pyridinamine;
N-(2-propenyl)-N-(1H-pyrrol-1-yl)-4-pyridinamine;
N-(2-propynyl)-N-(1H-pyrrol-1-yl)-4-pyridinamine;
N-(4-pyridinyl)-N-(1H-pyrrol-1-yl)-glycine ethyl ester;
N-[4-(piperidin-1-yl)-2-butynyl]-N-(1H-pyrrol-1-yl)-4-pyridinamine;
N-[4-(pyrrolidin-1-yl)-2-butynyl]-N-(1H-pyrrol-1-yl)-4-pyridinamine;
N-(2-chloro-1H-pyrrol-1-yl)-N-methyl-4-pyridinamine;
N-(2-chloro-1H-pyrrol-1-yl)-N-(4-pyridinyl)carbamic acid ethyl ester;
N-(2-chloro-1H-pyrrol-1-yl)-N-ethyl-4-pyridinamine;
N-(2-chloro-1H-pyrrol-1-yl)-N-propyl-4-pyridinamine;
1-[N-methyl-N-(3-nitro-4-pyridinyl)]aminopyrrole-3-carboxaldehyde;
1-[N-methyl-N-(4-pyridinyl)]aminopyrrole-3-carboxaldehyde;
1-[N-methyl-N-(4-pyridinyl)]aminopyrrole-2-carboxaldehyde;

1-[N-ethyl-N-(4-pyridinyl)]aminopyrrole-2-carboxaldehye;

1-[N-ethyl-N-(4-pyridinyl)]aminopyrrole-3-carboxaldehyde;

1-[N-propyl-N-(4-pyridinyl)]aminopyrrole-3-carboxaldehyde;

1-[N-propyl-N-(4-pyridinyl)]aminopyrrole-2-carboxaldehyde;

N-(2-formyl-1H-pyrrol-1-yl)-N-(4-pyridinyl)-carbamic acid ethyl ester;

α-methyl-1-[[N-(4-pyridinyl)-N-methyl]amino]-1H-pyrrole-2-methanol;

α-ethyl-1-[[N-(4-pyridinyl)-N-methyl]amino]-1H-pyrrole-2-methanol;

α-propyl-1-[[N-(4-pyridinyl)-N-methyl]amino]-1H-pyrrole-2-methanol;

α-methyl-1-[[N-ethyl-N-(4-pyridinyl)]amino]-1H-pyrrole-2-methanol;

α-methyl-1-[[N-methyl-N-(4-pyridinyl)]amino]-1H-pyrrole-3-methanol;

α-methyl-1-[[N-ethyl-N-(4-pyridinyl)]amino]-1H-pyrrole-3-methanol;

N-(2-chloro-1H-pyrrol-1-yl)-4-pyridinamine;

1-[N-(4-pyridinyl)]aminopyrrole-2-carboxaldehyde;

4-[N-(1H-pyrrol-1-yl)amino]-3-pyridinamine;

4-[[N-methyl-N-(1H-pyrrol-1-yl)amino]]-3-pyridinamine;

N-[3-[4-[[N-methyl-N-(1H-pyrrol-1-yl)]amino]]-pyridinyl]formamide;

2-butyl-N-methyl-N-(1H-pyrrol-1-yl)-4-pyridinamine;

N-(4-nitrophenyl)-N-(1H-pyrrol-1-yl)-4-pyridinamine;

1-[N-methyl-N-(4-pyridinyl)amino]-1H-pyrrole-2-methanol;

N-(2-methoxymethyl-1H-pyrrol-1-yl)-N-methyl-4-pyridinamine;

N-(2-ethenyl-1H-pyrrol-1-yl)-N-methyl-4-pyridinamine;

N-[2-(1-propenyl)-1H-pyrrol-1-yl]-N-methyl-4-pyridinamine;

N-[2-(2-phenylethenyl)-1H-pyrrol-1-yl]-N-methyl-4-pyridinamine;

N-[2-(2-methoxyethenyl)-1H-pyrrol-1-yl]-N-methyl-4-pyridinamine;

N-(2-ethyl-1H-pyrrol-1-yl)-N-methyl-4-pyridinamine;

N-methyl-N-(2-propyl-1H-pyrrol-1-yl)-4-pyridinamine;

N-methyl-N-(2-phenylethyl-1H-pyrrol-1-yl)-4-pyridinamine;

4-nitro-N-(1H-pyrrol-1-yl)-3-pyridinamine N-oxide;

N-methyl-N-(1H-pyrrol-1-yl)-4-nitro-3-pyridinamine N-oxide;

3-[N-methyl-N-(1H-pyrrol-1-yl)]-3,4-pyridinediamine;

N-(2-cyano-1H-pyrrol-1-yl)-N-methyl-4-pyridinamine;

N-methyl-N-(2-methyl-1H-pyrrol-1-yl)-4-pyridinamine;

N-propyl-N-(2-methyl-1H-pyrrol-1-yl)-4-pyridinamine;

N-methyl-N-(2,5-dimethyl-1H-pyrrol-1-yl)-4-pyridinamine;

N-methyl-N-[2-[2-(2-methylphenyl)ethenyl]-1H-pyrrol-1-yl]-4-pyridinamine;

N-ethyl-N-[2-[2-(4-methylphenyl)ethenyl]-1H-pyrrol-1-yl]-4-pyridinamine;

N-methyl-N-[2-[2-(2-methoxyphenyl)ethenyl]-1H-pyrrol-1-yl]-4-pyridinamine;

N-propyl-N-[2-[2-(3-methoxyphenyl)ethenyl]-1H-pyrrol-1-yl]-4-pyridinamine;

N-methyl-N-[2-[2-(4-methoxyphenyl)ethenyl]-1H-pyrrol-1-yl]-4-pyridinamine;

N-methyl-N-[2-[2-(2-chlorophenyl)ethenyl]-1H-pyrrol-1-yl]-4-pyridinamine;

N-methyl-N-[2-[2-(4-chlorophenyl)ethenyl]-1H-pyrrol-1-yl]-4-pyridinamine;

N-methyl-N-[2-[2-(3-thienyl)ethenyl]-1H-pyrrol-1-yl]-4-pyridinamine;

N-methyl-N-[2-[2-(2-methylphenyl)ethyl]-1H-pyrrol-1-yl]-4-pyridinamine;

N-ethyl-N-[2-[2-(3-methylphenyl)ethyl]-1H-pyrrol-1-yl]-4-pyridinamine;

N-propyl-N-[2-[2-(3-methoxyphenyl)ethyl]-1H-pyrrol-1-yl]-4-pyridinamine;

N-methyl-N-[2-[2-(4-methoxyphenyl)ethyl]-1H-pyrrol-1-yl]-4-pyridinamine;

N-ethyl-N-[2-[2-(2-chlorophenyl)ethyl]-1H-pyrrol-1-yl]-4-pyridinamine;

N-methyl-N-[2-[2-(4-chlorophenyl)ethyl]-1H-pyrrol-1-yl]-4-pyridinamine;

N-methyl-N-[2-[2-(3-thienyl)ethyl]-1H-pyrrol-1-yl]-4-pyridinamine;

N-(1H-pyrrol-1-yl)-3-pyridinamine; and
N-methyl-N-(1H-pyrrol-1-yl)-3-pyridinamine.

EXAMPLE 1

N-(1H-Pyrrol-1-yl)-4-pyridinamine

A solution of 4-chloropyridine (15 g) and N-aminopyrrole (18 g) in 225 ml of diglyme was stirred at 150° C. for one hour and thereafter cooled, diluted with water and basified with sodium carbonate. The mixture was extracted with ethyl acetate, and the organic extract was dried over anhydrous magnesium sulfate, filtered and evaporated to an oil. This oil was purified by high performance liquid chromatography (HPLC hereafter) using silica gel and ethyl acetate to give 12 g of a solid, mp 150° C. Five grams of the solid was recrystallized twice from benzene to give 2.8 g of crystals, mp 153°–154° C.

ANALYSIS:

Calculated for $C_9H_9N_3$: 67.90%C, 5.70%H, 26.40%N,

Found: 67.53%C, 5.81%H, 26.18%N,

EXAMPLE 2

N-methyl-N-(1H-pyrrol-1-yl)-3-nitro-4-pyridinamine hydrochloride

A solution of N-methylaminopyrrole (8.8 g) and 4-chloro-3-nitropyridine (14.5 g) in 200 ml of dimethylformamide was stirred at ambient temperature for 17 hours.

The reaction mixture was then added to an aqueous sodium bicarbonate solution and extracted with diethyl ether (2X). The combined organics were washed with water (3X) and dried (saturated sodium chloride solution, anhydrous magnesium sulfate). This was concentrated to 19.4 g of a solid. This was triturated with hexane to give 15.6 g of solid, mp 91°–99° C.

A 5.0 g portion of this material was converted into its hydrochloride salt via ethereal hydrochloric acid to give 5.6 g of a solid, m.p.: begins darkening @ 165° C., 234°–238° C. This was twice recrystallized from isopropanol:methanol (3:1) to give 3.4 g of a solid, m.p.: begins darkening @ 210° C., 235°–236° C., decomp.

Analysis:

Calculated for $C_{19}H_{10}N_4O_2 \cdot HCl$: 47.16%C, 4.35%H, 22.00%N,

Found: 47.07%C, 4.19%H, 22.09%N,

EXAMPLE 3

3-Nitro-N-(1H-pyrrol-1-yl)-4-pyridinamine hydrochloride

A solution of 2,5-dimethoxytetrahydrofuran (5.8 g) in 100 ml of glacial acetic acid was heated to 110° C. in an oil bath. To this was slowly added a solution of 4-hydrazino-3-nitropyridine (5.6 g in 300 ml of glacial acetic acid). The solution was heated an additional 0.5 hr.

The mixture was then concentrated to a solid and taken up in aqueous $Na_2CO_3$. This was extracted with ethyl ether (3X). The organics were then washed with water (1X) and dried (saturated sodium chloride solution, anhydrous sodium sulfate). This was then concentrated to a solid.

The pyrrole was purified via flash chromatography (ether/hexane) to yield 3.1 g of a solid, m.p. 138°–143° C. This was converted to the hydrochloride salt in ethyl ether to give 3.1 g of a solid, m.p. 228°–232° C. d. This was recrystallized from isopropanol:methanol (5:1) to give 2.2 g of a solid, m.p. 235°–238° C., decomp.

ANALYSIS

Calculated for $C_9H_8N_4O_2 \cdot HCl$: 44.92%C, 3.77%H, 23.28%N,

Found: 44.54%C, 3.73%H, 23.06%N,

EXAMPLE 4

N-(4-Pyridinyl)-N-(1N-pyrrol-1-yl)-N'-methylurea

A solution containing 4 g of N-(1H-pyrrol-1-yl)-4-pyridinamine and 1.6 g of methyl isocyanae in 125 ml of benzene was stirred at 50° C. for two hours, and thereafter cooled and evaporated to 6 g of a solid. This material was purified by HPLC (silica gel, 50% ethyl acetate in dichloromethane) to give 5 g of a solid, mp 156°–160° C. This material was recrystallized twice from benzene to give 2.6 g of crystals, mp 162°–163° C.

Analysis:

Calculated for $C_{11}H_{12}N_4O$: 61.09%C, 5.59%H, 25.91%N,

Found: 61.19%C, 5.67%H, 25.89%N.

EXAMPLE 5

N-(4-Pyridinyl)-N-(1H-pyrrol-1-yl)carbamic acid ethyl ester

To a solution containing 9 g of N-(1H-pyrrol-1-yl)-4-pyridinamine and 15 g of sodium bicarbonate in 350 ml of dichloromethane was added a solution containing 6.7 g of ethyl chloroformate in 50 ml of dichloromethane.

After stirring twenty hours at ambient temperature, the reaction mixture was washed with water and saturated sodium chloride and thereafter dried over anhydrous magnesium sulfate, filtered and evaporated to 12 g of an oil. This oil was purified by HPLC (silica gel, 20% ethyl acetate in dichloromethane) to give 10 g of a solid. This material was recrystallized from petroleum ether to give long needles, mp 54°–56° C.

Analysis:

Calculated for $C_{12}H_{13}N_3O_2$: 62.32%C, 5.67%H, 18.17%N,

Found: 62.07%C, 5.56%H, 18.32%N.

EXAMPLE 6

N-(4-Pyridinyl)-N-(1H-pyrrol-1-yl)propanamide

To a solution containing 2.9 g of N-(1H-pyrrol-1-yl)-4-pyridinamine and 5 g of sodium bicarbonate in 100 ml of dichloromethane was added a solution containing 1.9 g of propionyl chloride in 20 ml of dichloromethane.

After stirring twenty hours at ambient temperature, the reaction mixture was washed with water and saturated sodium chloride and thereafter dried over anhydrous magnesium sulfate, filtered and evaporated to 4.5 g of a solid. This material was purified by HPLC (silica gel, 15% ethyl acetate in dichloromethane) to give 3.3 g of a solid. This material was distilled via a Kugelrohr apparatus to give 2.9 g of crystals, mp 80°–82° C., bp 130°–135° C. @ 0.1 mm Hg.

Analysis:

Calculated for $C_{12}H_{13}N_3O$: 66.95%C, 6.09%H, 19.53%N,

Found: 66.98% C, 6.33%H, 19.49%N,

EXAMPLE 7

N-(4-Pyridinyl)-N-(1H-pyrrol-1-yl)linoleamide

A solution of linoleic acid (7 g) and thionyl chloride (5 g) in 25 ml of benzene was stirred at 80° for four hours, and thereafter cooled and evaporated to 8 g of an oil. To a solution of linoleic acid chloride in 200 ml of dichloromethane containing sodium bicarbonate (7 g) was added N-(1H-pyrrol-1-yl)-4-pyridinamine (4 g). After stirring twenty hours at ambient temperature the reaction mixture was washed with water and saturated sodium chloride and thereafter dried over magnesium sulfate, filtered and evaporated to 11 g of an oil. This oil was purified by HPLC (silica gel, 7% ethyl acetate in dichloromethane) to give 8.3 g of an oil. This oil was purified by column chromatography (alumina, ether) to give 5.1 g of an oil.

ANALYSIS

Calculated for $C_{27}H_{39}N_3O$: 76.91%C, 9.32%H, 9.97%N,

Found: 76.78%C, 9.41%H, 9.75%N.

EXAMPLE 8

N-(2-Chloro-1H-pyrrol-1-yl)-N-(4-pyridinyl)-linoleamide 2-naphthalene sulfonate A solution of linoleic acid (10 g) and thionyl chloride (6.4 g) in 75 ml of benzene was stirred for two hours at 85°, and thereafter cooled and evaporated to 12 g of an oil. To a solution of the acid chloride in 100 ml of dichloromethane was added sodium bicarbonate (5 g) and then 4-[N-(2-chloro-1H-pyrrol-1-yl)]aminopyridine (3.8 g). After stirring overnight at ambient temperature the reaction mixture was washed with water and saturated sodium chloride solution and thereafter dried over anhydrous magnesium sulfate, filtered and evaporated to 14 g of an oil. This oil was purified by high-pressure liquid chromatography (silica, 4% ethyl acetate in dichloromethane) to give 6.6 g of an oil. This oil was purified by column chromatography (alumina, ether) to give 5.9 g of an oil. A 2.3 g portion of the oil was converted to the 2-naphthalene sulfonate in ether, collected and dried to give 2.7 g of a solid, mp 127°–128° C.

Analysis:

Calculated for $C_{27}H_{38}ClN_3O \cdot C_{10}H_8SO_3$: 66.89%C, 6.98%H, 6.33%N, Found: 67.08%C, 7.02%H, 6.34%N,

EXAMPLE 9

N-(4-Pyridinyl)-N-(1H-pyrrol-1-yl)-phenylacetamide hydrochloride

To a solution of N-(1H-pyrrol-1-yl)-4-pyridinamine (6 g) in 400 ml of dichloromethane containing sodium bicarbonate (6.3 g) was added a solution of phenylacetyl chloride (6.7 g) in 50 ml of dichloromethane. After stirring four hours at ambient temperature, the reaction mixture was evaporated, stirred with water and extracted with ether. The organic extract was washed with water and saturated sodium chloride solution, dried over anhydrous magnesium sulfate, filtered and evaporated to 11 g of an oil. This oil was purified by flash chromatography (silica, 25% ethyl acetate in dichloromethane) to give 10 g of an oil. This oil was converted to the hydrochloride salt in ethanol to give 10.4 g of crystals, d 203°–205°. A 3 g sample was recrystallized from ethanol-ether to give 2.8 g of needles, d 203°–204°.

Analysis:
Calculated for $C_{17}H_{15}N_3O \cdot HCl$: 65.07%C, 5.14%H, 13.39%N,
Found: 65.31%C, 5.36%H, 13.72%N.

EXAMPLE 10

3,4-Dimethoxy-N-(4-pyridinyl)-N-(1H-pyrrol-1-yl)phenyl-acetamide hydrochloride

To a suspension of (3,4-dimethoxyphenyl)acetic acid (10 g) in 75 ml of benzene was added thionyl chloride (12 g). The resultant solution was stirred at 80° for three hours, and thereafter cooled and evaporated to 10.5 g of an oil.

To a solution of the acid chloride (5 g) in 150 ml of dichloromethane containing sodium bicarbonate (5 g) was added N-(1H-pyrrol-1-yl)-4-pyridinamine (3 g). After stirring twenty hours at ambient temperature the reaction mixture was washed with water and saturated sodium chloride and thereafter dried over anhydrous magnesium sulfate, filtered and evaporated to 6.5 g of an oil. This oil was purified by HPLC (silica, 20% ethyl acetate in dichloromethane) to give 4.1 g of the desired product as a solid, mp 98°–99° C. This material was dissolved in 25 ml of warm isopropanol, filtered and acidified by the addition of ethereal hydrochloric acid. The crystals which formed upon cooling were collected and dried to give 4.2 g of crystals, mp 212°–213° C.

Analysis:
Calculated for $C_{19}H_{19}N_3O_3 \cdot HCl$: 61.04%C, 5.39%H, 11.24%N,
Found: 61.03%C, 5.61%H, 11.00%N.

EXAMPLE 11

N-(2-Chloro-1H-pyrrol-1-yl)-N-(4-pyridinyl)-3,4-dimethoxy-phenylacetamide hydrochloride A solution of (3,4-dimethoxyphenyl)acetic acid (3 g) and thionyl chloride (4 g) in 25 ml of benzene was stirred one hour at reflux and thereafter cooled and evaporated to an oil. To a solution of the acid chloride (3.5 g) in 50 ml of dichloromethane was added sodium bicarbonate (5 g) and N-(2-chloro-1H-pyrrol-1-yl)]-4-pyridinamine (2.3 g). After stirring three hours at ambient temperature, the reaction mixture was evaporated, stirred with 300 ml of water and extracted with ether. The organic extract was washed with water and saturated sodium chloride and thereafter dried over anhydrous magnesium sulfate, filtered and evaporated to 4 g of an oil. This oil was purified by HPLC (silica, 20% ethyl acetate in dichloromethane) to give 3.4 g of an oil. This oil was dissolved in 25 ml of warm isopropanol, and filtered and thereafter converted to the hydrochloride salt by the addition of ethereal hydrochloric acid. The crystals which formed upon cooling and dilution with ether were collected and dried to give 3.3 g of a solid, mp 153°–154° C.

Analysis:
Calculated for $C_{19}H_{18}ClN_3O_3 \cdot HCl$: 55.89%C, 4.69%H, 10.29%N,
Found: 55.63%C, 4.69%H, 10.36%N.

EXAMPLE 12

N-Methyl-N-(1H-pyrrol-1-yl)-4-pyridinamine hydrochloride

To an ice-cooled suspension containing 1.5 g of sodium hydride in 5 ml of dimethylformamide was slowly dropped a solution of N-(1H-pyrrol-1-yl)-4-pyridinamine (4 g) in 10 ml of dimethylformamide. After the initial brisk hydrogen evolution subsided, the reaction mixture was slowly warmed to ambient temperature and thereafter warmed at 50° C. for thirty minutes. The reaction mixture was again cooled with an ice bath and a solution of dimethyl sulfate (3.8 g) in 5 ml of dimethylformamide was slowly added.

After thirty minutes, the reaction mixture was stirred with 300 ml of ice water and extracted with dichloromethane. The organic extract was washed with water and saturated sodium chloride and thereafter dried over anhydrous magnesium sulfate, filtered and evaporated to 4 g of an oil. This oil was purified by HPLC (silica gel, ethyl acetate) to give 3.5 g of an oil. This oil was dissolved in 10 ml of warm isopropanol and filtered, and thereafter converted to the hydrochloride salt by the addition of ethereal hydrochloric acid. The crystals which formed upon cooling were collected and dried to give 3.1 g of crystals, mp 226°–227° C. These crystals were sublimed at 135°–150° C. @ 0.01 mm Hg to give 2.9 g of crystals, mp 226°–227° C.

Analysis:
Calculated for $C_{10}H_{11}N_3 \cdot HCl$: 57.28%C, 5.77%H, 20.04%N,
Found: 57.39%C, 5.78%H, 19.99%N.

EXAMPLE 13

N-Ethyl-N-(1H-pyrrol-1-yl)-4-pyridinamine hydrochloride

A solution of N-(1H-pyrrol-1-yl)-4-pyridinamine (4 g) in 20 ml of dimethylformamide was slowly added dropwise to an ice-cooled suspension containing 1.2 g of sodium hydride in 5 ml of dimethylformamide. After the initial brisk reaction subsided, the mixture was stirred cold for thirty minutes, and thereafter a solution of diethyl sulfate (4.3 g) in 10 ml of dimethylformamide was added. After stirring twenty hours at ambient temperature, the reaction mixture was quenched with 500 ml of water and extracted with dichloromethane. The organic extract was washed with water and saturated sodium chloride and thereafter dried over anhydrous magnesium sulfate, filtered and evaporated to 4.3 g of an oil. This oil was purified by HPLC (silica, ethyl acetate) to give 3.7 g of an oil. This oil was dissolved in 10 ml of warm isopropanol, filtered, and acidified by the addition of ethereal HCl. The product which formed upon cooling was collected and dried to give 3.3 g of a solid, mp 224°–225° C.

Analysis:

Calculated for $C_{11}H_{13}N_3 \cdot HCl$: 59.06%C, 6.31%H, 18.79%N,

Found: 58.84%C, 6.52%H, 18.61%N.

EXAMPLE 14

N-Propyl-N-(1H-pyrrol-1-yl)-4-pyridinamine hydrochloride

A solution of N-(1H-pyrrol-1-yl)-4-pyridinamine (3 g) in 25 ml of dimethylformamide was slowly dropped into a suspension containing 1 g of sodium hydride in 5 ml of dimethylformamide. After the anion formation, the reaction mixture was cooled with an ice bath and a solution of 1-bromopropane (2.8 g) in 5 ml of dimethylformamide was slowly added. After stirring one hour, the reaction mixture was quenched with water and extracted with dichloromethane. The organic extract was washed with water and saturated sodium chloride solution, and thereafter dried over anhydrous magnesium sulfate, filtered and evaporated to an oil. This oil was purified by flash chromatography (silica, ethyl acetate) to give 5 g of an oil. This oil was converted to the hydrochloride salt in warm isopropanol. The crystals which formed upon dilution with ether were collected and dried to give 3.3 g of a solid, d 230°–232° C. This material was recrystallized from isopropanol-ether to give 2.6 g of crystals, d 232°–233° C.

Analysis:

Calculated for $C_{12}H_{15}N_3 \cdot HCl$: 60.62%C, 6.78%H, 17.68%N,

Found: 60.70%C, 6.88%H, 17.67%N.

EXAMPLE 15

N-Phenylmethyl-N-(1H-pyrrol-1-yl)-4-pyridinamine hydrochloride

A solution of N-(1H-pyrrol-1-yl)-4-pyridinamine (4 g) in 20 ml of dimethylformamide was slowly added to an ice-cooled stirred suspension containing 1.1 g of sodium hydride in 5 ml of dimethylformamide. After the anion formation, a solution of benzylbromide (4.7 g) in 10 ml of dimethyformamide was slowly added. After stirring thirty minutes, the reaction mixture was stirred with 500 ml of ice water and extracted with ether. The organic extract was washed with water and saturated sodium chloride solution thereafter and dried over anhydrous magnesium sulfate, filtered and evaporated to 6 g of an oil. This material was purified by flash chromatography (silica, ethyl acetate) to give 4.4 g of the product as a solid, mp 77°–79° C. This material was converted to the hydrochloride salt in 20 ml of warm ethanol by the addition of ethereal HCl. The crystals which formed upon cooling and dilution with ether were collected and dried to give 3.1 g of white crystals, mp 210°–211° C.

Analysis:

Calculated for $C_{16}H_{15}N_3 \cdot HCl$: 67.24%C, 5.64%H, 14.71%N,

Found: 67.15%C, 5.675H, 14.76%N.

EXAMPLE 16

N-(Butyl)-N-(1H-pyrrol-1-yl)-4-pyridinamine hydrochloride

A solution of N-(1H-pyrrol-1-yl)-4-pyridinamine (4 g) in 20 ml of dimethylformamide was slowly added to an ice-cooled suspension of sodium hydride (60% oil dispersion, 1.1 g) in 5 ml of dimethylformamide. After the anion formation, a solution of 1-bromobutane (3.8 g) in 10 ml of dimethylformamide was slowly added. After thirty minutes, the reaction mixture was stirred with 300 ml of ice-water and extracted with ethyl acetate. The organic extract was washed with water and saturated sodium chloride solution, dried over anhydrous magnesium sulfate, filtered and evaporated to 5.5 g of an oil. This material was purified by HPLC (silica, ethyl acetate) to give 4.6 g of an oil. This oil was converted to the hydrochloride salt in 20 ml of warm isopropanol. The product which precipitated upon cooling was collected and dried to give 3.8 g of crystals, mp 178°–179°.

Analysis:

Calculated for $C_{13}H_{17}N_3 \cdot HCl$: 62.02%C, 7.21%H, 16.69%N,

Found 62.03%C, 7.27%H, 16.61%N.

EXAMPLE 17

N-(2-Propenyl)-N-(1H-pyrrol-1-yl)-4-pyridinamine hydrochloride

To an ice-cooled suspension of sodium hydride (60% oil dispersion, 1.2 g, previously washed with hexanes) in 5 ml of dimethylformamide was slowly added a solution of N-(1H-pyrrol-1-yl)-4-pyridinamine (4 g) in 25 ml of dimethylformamide. After the anion formation, a solution of allyl bromide (3.1 g) in 5 ml of dimethylformamide was added. After stirring cold for one hour, the reaction mixture was stirred with water and extracted with ethyl acetate. The organic extract was washed with water and saturated sodium chloride solution, dried over anhydrous magnesium sulfate, filtered and evaporated to 6 g of an oil. This oil was purified by flash chromatography (silica, ethyl acetate) to give 5 g of an oil. This oil was converted to the hydrochloride salt and twice recrystallized from isopropanol/ether to give 3.5 g of crystals, mp 218°–219°.

Analysis:

Calculated for $C_{12}H_{13}N_3 \cdot HCl$: 61.14%C, 5.99%H, 17.83%N,

Found: 61.04%C, 6.16%H, 17.78%N.

EXAMPLE 18

N-(2-Propynyl)-N-(1H-pyrrol-1-yl)-4-pyridinamine hydrochloride

To an ice-cold suspension of sodium hydride (60% oil dispersion, 3 g) in 10 ml of dimethylformamide was slowly added N-(1H-pyrrol-1-yl)-4-pyridinamine (10 g) in 70 ml of dimethylformamide. After the anion formation, a solution of propargyl bromide (80 wt. % in toluene, 11 g) in 10 ml of dimethylformamide was slowly added. After one hour, the reaction mixture was stirred with 500 ml of ice-water and extracted with ethyl acetate. The organic extract was washed with water and saturated sodium chloride solution, dried over anhydrous magnesium sulfate, filtered and evaporated to 20 g of oil. This oil was purified by HPLC (silica, ethyl acetate-dichloromethane) to give 12 g of oil. A four gram sample was converted to the hydrochloride salt in 30 ml of warm isopropanol to yield, upon cooling, 3.3 g of solid, d 224°–225°. This material was recrystallized from isopropanol to give 2.7 g of solid, d 230°–231°.

Analysis:

Calculated for $C_{12}H_{11}N_3 \cdot HCl$: 61.67%C, 5.18%H, 17.98%N,

Found: 61.41%C, 5.10%H, 17.88%N.

EXAMPLE 19

N-(4-Pyridinyl)-N-(1H-pyrrol-1-yl)-glycine ethyl ester hydrochloride

A solution of N-(1H-pyrrol-1-yl)-4-pyridinamine (5 g) in 25 ml of dimethylformamide was slowly added to a suspension of sodium hydride (60% oil dispersion, 1.4 g, washed with hexane) in 5 ml of dimethylformamide. After the anion formation, the mixture was cooled with an ice-salt bath, and a solution of ethyl chloroacetate (4.2 g) in 5 ml of dimethylformamide was slowly added. After thirty minutes, the mixture was stirred with ice water and extracted with dichloromethane. The organic extract was washed with water and saturated sodium chloride solution, dried over anhydrous magnesium sulfate, filtered and evaporated to 8 g of oil. This oil was purified by HPLC (silica, ethyl acetate) to give 4.1 g of solid, mp 92°–95°. This material was converted to the hydrochloride salt and recrystallized twice from isopropanol and once from ethanol to give 2.6 g of crystals, d 240°–241°.

Analysis:
Calculated for $C_{13}H_{15}N_3O_2 \cdot HCl$: 55.42%C, 5.72%H, 14.92%N,
Found: 55.40%C, 5.68%H, 14.96%N.

EXAMPLE 20

N-[4-(Piperidin-1-yl)-2-butynyl]-N-(1H-pyrrol-1-yl)-4-pyridinamine dihydrochloride A mixture of N-(2-propynyl)-N-(1H-pyrrol-1-yl)-4-pyridinamine (4 g), piperidine (2 g), paraformaldehyde (4 g) and cuprous chloride (0.1 g) in 30 ml of dioxane was warmed on a steam bath for 30 minutes and thereafter cooled, diluted with ethyl acetate and filtered. The filtrate was evaporated to 8 g of oil which was purified by HPLC (silica, 10% methanol in ethyl acetate) to give 3.7 g of oil. This oil was converted to the dihydrochloride salt and recrystallized from isopropanol and from ethanol-ether to give 2.8 g of crystals, d 224°–225°.

Analysis:
Calculated for $C_{18}H_{22}N_4 \cdot 2HCl$: 58.85%C, 6.59%H, 15.26%N,
Found: 58.51%C, 6.64%H, 15.18%N.

EXAMPLE 21

N-[4-(Pyrrolidin-1-yl)-2-butynyl]-N-(1H-pyrrol-1-yl)-4-pyridinamine dihydrochloride A mixture of N-(2-propynyl)-N-(1H-pyrrol-1-yl)-4-pyridinamine (4 g), pyrrolidine (1.6 g), paraformaldehyde (6 g) and cuprous chloride (0.1 g) in 30 ml of dioxane was warmed on a steam bath for thirty minutes and thereafter cooled, stirred with water, extracted with dichloromethane, filtered and separated. The organic extract was dried over anhydrous magnesium sulfate, filtered and evaporated to 5.9 g of oil. This oil was purified by HPLC (silica, 10% methanol in dichloromethane) to give 3 g of oil. This oil was converted to the dihydrochloride salt and twice recrystallized from isopropanol to give 3.2 g of crystals, d 226°–227°.

Analysis:
Calculated for $C_{17}H_{20}N_4 \cdot 2HCl$: 57.79%C, 6.28%H, 15.86%N,
Found: 57.64%C, 6.25%H, 15.94N.

EXAMPLE 22

N-(2-Chloro-1H-pyrrol-1-yl)-N-methyl-4-pyridinamine hydrochloride

To a solution of N-Methyl-N-(1H-pyrrol-1-yl)-4-pyridinamine (7.7 g) in 300 ml of anhydrous tetrahydrofuran cooled to 5° with an ice bath was added N-chlorosuccinimide (5.2 g). The reaction mixture was stirred sixty hours at ambient temperature, and thereafter additional NCS (0.9 g) was added. After stirring an additional sixteen hours at ambient temperature, the reaction mixture was stirred with an aqueous solution of sodium bisulfite and extracted with ether. The organic extract was washed with water and saturated sodium chloride and thereafter dried over anhydrous magnesium sulfate, filtered and evaporated to 9.5 g of an oil. This oil was purified by HPLC (silica, ethyl acetate) to give 4.4 g of an oil. This oil was purified by column chromatography (alumina, ether) to give 2.4 g of the desired product as an oil. This oil was dissolved in 25 ml of isopropanol, filtered, and converted to the hyrochloride salt by the addition of ethereal hydrochloric acid. The solution was diluted with 25 ml of ether and cooled. The resultant precipitate was collected and dried to give 2.5 g of crystals, mp 230°–231° C.

Analysis:
Calculated for $C_{10}H_{10}ClN_3 \cdot HCl$: 49.20%C, 4.54%H, 17.22%N,
Found: 49.15%C, 4.67%H, 17.34%N.

EXAMPLE 23

N-(2-Chloro-1H-pyrrol-1-yl)-N-(4-pyridinyl)carbamic acid ethyl ester hydrochloride To a solution of N-(4-pyridinyl)-N-(1H-pyrrol-1-yl) carbamic acid ethyl ester (9 g) in 100 ml of anhydrous tetrahydrofuran warmed to 50° was slowly dropped a solution of N-chlorosuccinimide (5.2 g) in 75 ml of anhydrous tetrahydrofuran. After stirring seven hours at 50°, the reaction mixture was cooled, stirred with an aqueous solution of sodium bisulfite and extracted with ethyl acetate. The organic extract was washed with water and saturated sodium chloride and thereafter dried over anhydrous magnesium sulfate, filtered and evaporated to 11.5 g of an oil. This oil was purified by HPLC (silica, 20% ethyl acetate in dichloromethane) to give 3.8 g of the desired product as a solid. This material was converted to the hydrochloride salt and twice recrystallized from isopropanol-ether to give 3.3 g of crystals, d 139°–140° C.

Analysis:
Calculated for $C_{12}H_{12}ClN_3O_2 \cdot HCl$: 47.70%C, 4.34%H, 13.91%N,
Found 47.58%C, 4.36%H, 13.97%N.

EXAMPLE 24

N-(2-Chloro-1H-pyrrol-1-yl)-N-ethyl-4-pyridinamine hydrochloride

To a solution of N-ethyl-N-(1H-pyrrol-1-yl)-4-pyridinamine (10.2 g) in 200 ml of anhydrous tetrahydrofuran was added N-chlorosuccinimide (7.3 g). After stirring twenty hours at ambient temperature, the reaction mixture was stirred with an aqueous solution of sodium sulfite and extracted with dichloromethane. The organic extract was washed with water and saturated sodium chloride and thereafter dried over anhydrous magnesium sulfate, filtered and evaporated to 12 g of an oil. This oil was purified by HPLC (silica, 25% dichloromethane in ethyl acetate) to give 3.7 g of the desired product as an oil. This oil was converted to the hydrochloride salt and twice recrystallized from isopropanol-ether to give 3.1 g of crystals, mp 206°–207° C.

Analysis

Calculated for $C_{11}H_{12}ClN_3.HCl$: 51.18%C, 5.08%H, 16.28%N,

Found: 51.43%C, 4.95%H, 16.36%N.

EXAMPLE 25

N-(2-Chloro-1H-pyrrol-1-yl)-N-propyl-4-pyridinamine hydrochloride

To a solution of N-propyl-N-(1H-pyrrol-1-yl)-4-pyridinamine (11 g) in 250 ml of tetrahydrofuran, cooled with an ice bath, was added N-chlorosuccinimide (8 g) as a powder. The reaction mixture was warmed to ambient temperature and after sixteen hours additional N-chlorosuccinimide (1 g) was added. After stirring for additional three hours, the reaction mixture was stirred with cold water, basified with sodium carbonate and extracted with ethyl acetate. The organic extract was washed with water and saturated sodium chloride solution, dried over anhydrous magnesium sulfate, filtered and evaporated to 14 g of oil. This oil was purified by HPLC (silica, ethyl acetate-dichloromethane) to give 4.1 g of pure product as an oil. This oil was converted to the hydrochloride salt and recrystallized twice from isopropanol-ether to give 2.4 g of crystals, mp 210°–211°.

Analysis:

Calculated for $C_{12}H_{14}ClN_3.HCl$: 52.95%C, 5.56%H, 15.44%N,

Found: 52.76%C, 5.40%H, 15.25%N.

EXAMPLE 26

1[N-Methyl-N-(3-nitro-4-pyridinyl)]aminopyrrole-3-carboxaldehyde

To chilled dimethylformamide (5.5 ml) was slowly added $POCl_3$ (7.5 ml). This was stirred for 10 minutes at ambient temperature and diluted with 10 ml of 1,2-dichloroethane.

To this was added a solution of N-methyl-N-(1H-pyrrol-1-yl)-3-nitro-4-pyridinamine (12.0 g) in 125 ml of 1,2-dichloroethane. This was heated at 80° C. for 4.5 hours.

The reaction was quenched with 45 g of sodium acetate trihydrate dissolved to a total volume of 125 ml with water. This was refluxed for 1 hour, cooled and diluted with dichloromethane. The layers were separated and the aqueous phase was extracted with dichloromethane (2×). The combined organics were then washed with a saturated $Na_2CO_3$ solution and dried (saturated sodium chloride solution, anhydrous magnesium sulfate). This was concentrated to a semi-solid.

The aldehyde was purified via HPLC (10% ethyl acetate/dichloromethane) to yield 7.3 g of the 2-isomer and 2.35 g of the 3-isomer, mp 128°–142° C. The 3-isomer was recrystallized from isopropyl ether:methanol (5:1) to give 1.0 g of a solid, mp 145°–148° C.

Analysis:

Calculated for $C_{11}H_{10}N_4O_3$: 53.66%C, 4.09%H, 22.75%N,

Found: 53.23%C, 4.09%H, 22.73%N.

EXAMPLE 27

1-[N-Methyl-N-(4-pyridinyl)]aminopyrrole-3-carboxaldehyde maleate

To cold dimethylformamide (7 g) was slowly added phosphorous oxychloride (14.7 g). The resultant clear complex was stirred one hour at ambient temperature and thereafter dissolved in 25 ml of dichloroethane. To this cooled solution was slowly added a solution of N-methyl-N-(1H-pyrrol-1-yl)-4-pyridinamine (15 g) in 25 ml of dichloroethane. After stirring twelve hours at 95°, the reaction mixture was cooled, and a solution of sodium acetate trihydrate (60 g) in 200 ml of water was slowly added. The resultant mixture was stirred one hour at 95° and thereafter cooled, stirred with 500 ml of water and basified with sodium carbonate. The oil which separated was extracted with dichloromethane, washed with water and saturated sodium chloride and thereafter dried over anhydrous magnesium sulfate, filtered and evaporated to 18 g of an oil. This oil was purified by HPLC (silica, ethyl acetate) to give 10.2 g of the pyrrole-2-aldehyde as a solid, mp 71°–74° C. Further elution yielded 2 g of the pyrrole-3-aldehyde as an oil. This oil was converted to the maleate salt and recrystallized from isopropanol to give 1.9 g of crystals, mp 139°–140° C.

Analysis:

Calculated for $C_{11}H_{11}N_3O\ C_4H_4O_4$: 56.78%C, 4.77%H, 13.25%N,

Found: 56.64%C, 4.87%H, 13.20%N.

EXAMPLE 28

1-[N-Methyl-N-(4-pyridinyl)]aminopyrrole-2-carboxaldehyde maleate

To cold dimethylformamide (7 g) was slowly added phosphorous oxychloride (14.7 g). The resultant clear complex was stirred one hour at ambient temperature and thereafter dissolved in 25 ml of dichloroethane. To this cooled solution was slowly added a solution of N-methyl-N-(1H-pyrrol-1-yl)-4-pyridinamine (15 g) in 25 ml of dichloroethane. After stirring twelve hours at 95°, the reaction mixture was cooled, and a solution of sodium acetate trihydrate (60 g) in 200 ml of water was slowly added. The resultant mixture was stirred one hour at 95°, and thereafter cooled, stirred with 500 ml of water and basified with sodium carbonate. The oil which separated was extracted with dichloromethane, washed with water and saturated sodium chloride and thereafter dried over anhydrous magnesium sulfate, filtered and evaporated to 18 g of an oil. This oil was purified by HPLC (silica, ethyl acetate) to give 10.2 g of the pyrrole-2-aldehyde as a solid, mp 71°–74°. A 2.5 g portion of this solid was converted to the maleate salt and recrystallized from isopropanol to give 3.4 g of crystals, m.p. 118°–119° C.

Analysis:

Calculated for $C_{11}H_{11}N_3O.C_4H_4O_4$: 56.78%C, 4.77%H, 13.25%N,

Found: 56.79%C, 4.83%H, ° 13.22%N.

EXAMPLE 29

1-[N-Ethyl-N-(4-pyridinyl)]aminopyrrole-2-carboxaldehyde hydrochloride

To cold dimethylformamide (11.1 g) was slowly added phosphorous oxychloride (23.2 g). The resultant clear complex was stirred one hour at ambient temperature and thereafter a solution of N-ethyl-N-(1H-pyrrol- 1-yl)-4-pyridinamine (20.5 g) in 135 ml of dichloroethane was added. After stirring twelve hours at 95° the reaction mixture was cooled and hydrolyzed for one hour at 95° with a solution of sodium acetate trihydrate (40 g) in 150 ml of water. The reaction mixture was cooled, basified with sodium carbonate and extracted with dichloromethane. The organic extract was washed with water and saturated sodium chloride solution and thereafter dried over anhydrous magnesium sulfate, filtered and evaporated to 24 g of an oil. This oil was purified first by flash chromatography (silica, dichloromethane, then 10% ethyl acetate in dichloromethane), then by high-pressure liquid chromatography (silica, ethyl acetate) to give 8 g of the pyrrole-2-aldehyde as an oil and 8 g of the pyrrole-3-aldehyde as an oil. 2.5 g of the pyrrole-2-aldehyde was converted to the hydrochloride salt in 2-propanol to give 2.2 g of crystals, mp 214°–215° C.

Analysis:
Calculated for $C_{12}H_{13}N_3O \cdot HCl$: 57.26%C, 5.61%H, 16.70%N,
Found: 57.25%C, 5.76%H, 16.84%N.

EXAMPLE 30

1-[N-Ethyl-N-(4-pyridinyl)]aminopyrrole-3-carboxaldehyde maleate

To cold dimethylformamide (11.1 g) was slowly added phosphorous oxychloride (23.2 g). The resultant clear complex was stirred one hour at ambient temperature and thereafter a solution of N-ethyl-N-(1H-pyrrol-1-yl)-4-pyridinamine (20.5 g) in 135 ml of dichloroethane was added. After stirring twelve hours at 95° the reaction mixture was cooled and hydrolyzed for one hour at 95° with a solution of sodium acetate trihydrate (40 g) in 150 ml of water. The reaction mixture was cooled, basified with sodium carbonate and extracted with dichloromethane. The organic extract was washed with water and saturated sodium chloride solution and thereafter dried over anhydrous magnesium sulfate, filtered and evaporated to 24 g of an oil. This oil was purified first by flash chromatography (silica, dichloromethane, then 10% ethyl acetate in dichloromethane), then by high-pressure liquid chromatography (silica, ethyl acetate) to give 8 g of the pyrrole-2-aldehyde as an oil and 8 g of the pyrrole-3-aldehyde as an oil. 2.5 g of the pyrrole-3-aldehyde was converted to the maleate salt in 2-propanol to give 3.4 g of crystals, d 135°–136° C.

Analysis:
Calculated for $C_{12}H_{13}N_3O \cdot C_4H_4O_4$: 58.00%C, 5.17%H, 12.69%N,
Found: 58.04%C, 5.12%H, 12.67%N.

EXAMPLE 31

1-[N-Propyl-N-(4-pyridinyl)]aminopyrrole-3-carboxaldehyde maleate

To ice-cooled dimethylformamide (8.4 g) was slowly added phosphorous oxychloride (17.6 g). After the formation of reagent complex, a solution of N-propyl-N-(1H-pyrrol-1-yl)-4-pyridinamine (10.5 g) in 100 ml of dichloroethane was added. After stirring at 95° for six hours, the reaction mixture was hydrolyzed at 60° with a solution of sodium acetate trihydrate (10 g) in 25 ml of water. The mixture was cooled, basified with sodium carbonate and extracted with dichloromethane. The organic extract was washed with water and saturated sodium chloride solution, dried over anhydrous magnesium sulfate, filtered and evaporated to 10.5 g of oil. This oil was purified by HPLC (silica, ethyl acetate) to give 4.4 g of the 2-aldehyde and 4.4 g of the 3-aldehyde. The 3-aldehyde was purified by column chromatography (alumina, ether) to give 4 g of oil. This oil as converted to the maleate salt and recrystallized twice from isopropanol-ether to give 4.4 g of crystals, d 144°–146°.

Analysis
Calculated for $C_{13}H_{15}N_3O \cdot C_4H_4O_4$: 59.12%C, 5.55%H, 12.17%N,
Found: 59.01%C, 5.51%H, 12.13%N.

EXAMPLE 32

1-[N-Propyl-N-(4-pyridinyl)]aminopyrrole-2-carboxaldehyde maleate

To ice-cooled dimethylformamide (8.4 g) was slowly added phosphorous oxychloride (17.6 g). After the formation of reagent complex, a solution of N-propyl-N-(1H-pyrrol-1-yl)-4-pyridinamine (10.5 g) in 100 ml of dichloroethane was added. After stirring at 95° for six hours, the reaction mixture was hydrolyzed at 60° with a solution of sodium acetate trihydrate (10 g) in 25 ml of water. The mixture was cooled, basified with sodium carbonate and extracted with dichloromethane. The organic extract was washed with water and saturated sodium chloride solution, dried over anhydrous magnesium sulfate, filtered and evaporated to 10.5 g of oil. This oil was purified by HPLC (silica, ethyl acetate) to give 4.4 g of the 2-aldehyde and 4.4 g of the 3-aldehyde. The 2-aldehyde was purified by column chromatography (alumina, ether) to give 4 g of oil. This oil was converted to the maleate salt and recrystallized twice from isopropanol-ether to give 4 g of crystals, mp 95°–97°.

Analysis:
Calculated for $C_{13}H_{15}N_3O \cdot C_4H_4O_4$: 59.12%C, 5.55%H, 12.17%N,
Found 59.15%C, 5.53%H, 12.19%N.

EXAMPLE 33

N-(2-Formyl-1H-pyrrol-1-yl)-N-(4-pyridinyl)-carbamic acid ethyl ester maleate

To cold dimethylformamide (9 g) was slowly added phosphorous oxychloride (18 g). After the reagent complex was formed, a solution of N-(4-pyridinyl)-N-(1H-pyrrol-1-yl)-carbamic acid ethyl ester (11 g) in 100 ml of dichloroethane was added. After stirring eight hours at 90°, the reaction mixture was cooled, hydrolyzed with a solution of sodium acetate trihydrate (20 g) in 100 ml of water, basified with sodium carbonate and extracted with dichloromethane. The organic extract was washed with water and saturated sodium chloride solution, dried over anhydrous magnesium sulfate, filtered and evaporated to 14 g of an oil. This oil was purified by HPLC (silica, 20% ethyl acetate in dihcloromethane) to give 4 g of pure product which was converted to the maleate salt and recrystallized twice from isopropanol to give 3.4 g of needles, d 139°–140°.

Analysis:
Calculated for $C_{13}H_{13}N_3O_3 \cdot C_4H_4O_4$: 54.40%C, 4.57%H, 11.20%N,
Found: 54.24%C, 4.68%H, 11.19%N.

EXAMPLE 34

α-methyl-1-[[N-(4-pyridinyl)-N-methyl]amino]-1H-pyrrole-2-methanol maleate

To a cooled solution of 1-[N-methyl-N-(4-pyridinyl)]-aminopyrrole-2-carboxaldehyde (3 g) in 50 ml of anhydrous tetrahydrofuran was slowly dropped methylmagnesium bromide (3.2 M in ether, 5.1 ml). After stirring two hours at ambient temperature, the reaction mixture was stirred with 300 ml of saturated ammonium chloride and extracted with ethyl acetate. The organic extract was washed with water and saturated sodium chloride and thereafter dried over anhydrous magnesium sulfate, filtered and evaporated to 3.4 g of an oil. This oil was purified by HPLC (silica, 5% methanol in dichloromethane) to give 3.0 g of an oil. This oil was converted to the maleate salt and recrystallized from isopropanol-ether to give 3.6 g of crystals, mp 118°–119° C.

Analysis:
Calculated for $C_{12}H_{15}N_3O \cdot C_4H_4O_4$: 57.65%C, 5.75%H, 12.61%N,
Found: 57.66%C, 5.87%H, 12.39%N.

EXAMPLE 35

α-Ethyl-1-[[N-(4-pyridinyl)-N-methyl]amino]-1H-pyrrole-2-methanol

To a cooled solution of 1-[N-methyl-N-(4-pyridinyl)]-aminopyrrole-2carboxaldehyde (3.5 g) in 75 ml of tetrahydrofuran was slowly dropped a solution of ethylmagnesium bromide (2M in tetrahydrofuran, 10.5 ml). After thirty minutes the reaction mixture was stirred with 200 ml of saturated ammonium chloride solution, basified with sodium carbonate and extracted with ethyl acetate. The organic extract was washed with water and saturated sodium chloride solution and thereafter dried over anhydrous magnesium sulfate, filtered and evaporated to 4 g of an oil. This oil was crystallized from isopropyl ether to give 3 g of a solid, m.p. 86°–88° C.

Analysis:
Calculated for $C_{13}H_{17}N_3O$: 67.50%C, 7.41%H, 18.17%N,
Found: 67.23%C, 7.39%H, 18.06%N.

EXAMPLE 36

α-Propyl-1-[[N-(4-pyridinyl)-N-methyl]amino]-1H-pyrrole-2-methanol

To a cooled solution of 1-[N-methyl-N-(4-pyridinyl)]-aminopyrrole-2-carboxaldehyde (3.5 g) in 75 ml of tetrahydrofuran was slowly dropped a solution of propylmagnesium chloride (2M in ether, 10.5 ml). After thirty minutes the reaction mixture was stirred with saturated ammonium chloride solution, basified with sodium carbonate and extracted with ethyl acetate. The organic extract was washed with water and saturated sodium chloride solution and thereafter dried over anhydrous magnesium sulfate, filtered and evaporated to 4.5 g of an oil. This oil was crystallized from isopropyl ether to give 3.2 g of crystals, mp 98°–99° C.

Analysis:
Calculated for $C_{14}H_{19}N_3O$: 68.54%C, 7.81%H, 17.13%N,
Found: 68.49%C, 7.75%H, 17.23%N.

EXAMPLE 37

α-Methyl-1-[[N-ethyl-N-(4-pyridinyl)]amino]-1H-pyrrole-2-methanol

To an ice-cooled solution of 1-[N-ethyl-N-(4-pyridinyl)]-aminopyrrole-2-carboxaldehyde (3 g) in 75 ml of tetrahydrofuran was added methylmagnesium bromide (3.2 M in ether, 9 ml). After one hour, the reaction mixture was stirred with saturated ammonium chloride solution, basified with sodium carbonate and extracted with ethyl acetate. The organic extract was washed with water and saturated sodium chloride solution, dried over anhydrous magnesium sulfate, filtered and evaporated to 3 g of solid, mp 117°–121°. This material was recrystallized from isopropyl ether to give 2.6 g of crystals, mp 122°–123°.

Analysis:
Calculated for $C_{13}H_{17}N_3O$: 67.50%C, 7.41%H, 18.17%N,
Found: 67.38%C, 7.44%H, 18.07%N.

EXAMPLE 38

α-Methyl-1-[[N-methyl-N-(4-pyridinyl)]amino]-1H-pyrrole-3-methanol

To an ice-cooled solution of 1-[N-methyl-N-(4-pyridinyl)]-aminopyrrole-3-carboxaldehyde (3.5 g) in 50 ml of tetrahydrofuran was added methylmagnesium bromide (3.2 M in ether, 6 ml). After three hours, the reaction mixture was stirred with saturated ammonium chloride solution, basified with sodium carbonate and extracted with ethyl acetate. The organic extract was washed with water and saturated sodium chloride solution, dried over anhydrous magnesium sulfate, filtered and evaporated to 3.9 g of oil. This oil was purified by HPLC (silica, 5% methanol in dichloromethane) to give 2.8 g of waxy solid. This material was recrystallized from ether to give 2.1 g of solid, mp 95°–96°.

Analysis:
Calculated for $C_{12}H_{15}N_3O$: 66.33%C, 6.96%H, 19.34%N,
Found: 65.89%C, 6.84%H,° 19.14%N.

EXAMPLE 39

α-Methyl-1-[[N-ethyl-N-(4-pyridinyl)]amino]-1H-pyrrole-3-methanol

To an ice-cooled solution of 1-[N-ethyl-N-(4-pyridinyl)]-aminopyrrole-3-carboxaldehyde (3 g) in 100 ml of tetrahydrofuran was added methylmagnesium bromide (3.2 M in ether, 9 ml). After one hour, the reaction mixture was stirred with saturated ammonium chloride solution, basified with sodium carbonate and extracted with ethyl acetate. The organic extract was washed with water and saturated sodium chloride solution, dried over anhydrous magnesium sulfate, filtered and evaporated to 2.8 g of oil. This oil was purified by HPLC (silica, 5% methanol in ethyl acetate) to give 2.6 g of oil. This oil was crystallized from ether to give 1.7 g of solid, mp 87°–89°.

Analysis:
Calculated for $C_{13}H_{17}N_3O$: 67.50%C, 7.41%H, 18.17%N,
Found: 67.70%C, 7.42%H, 18.35%N.

EXAMPLE 40

N-(2-Chloro-1H-pyrrol-1-yl)-4-pyridinamine hydrochloride

A mixture prepared from a solution of N-(2-chloro-1H-pyrrol-1-yl)-N-(4-pyridinyl)carbamic acid ethyl ester (6 g) in 50 ml of ethanol and 20 ml of 10% aqueous sodium hydroxide solution was warmed for 15 minutes on a steam bath, and thereafter cooled, diluted with 500 ml of water and extracted with dichloromethane. The organic extract was washed with water and saturated sodium chloride and thereafter dried over anhydrous magnesium sulfate, filtered and evaporated to 5 g of an oil. This oil was purified by HPLC (silica, ethyl acetate) to give 3.5 g of a solid, mp 115°–118° C. This material was converted to the hydrochloride salt and recrystallized twice from isopropanol-ether to give 3.4 g of crystals, mp 172°–173° C.

Analysis

Calculated for $C_9H_8ClN_3 \cdot HCl$: 46.98%C, 3.94%H, 18.27%N,

Found: 46.76%C, 3.80%H, 18.13N.

EXAMPLE 41

1-[N-(4-Pyridinyl)]aminopyrrole-2-carboxaldehyde maleate

A solution prepared from N-(2-formyl-1H-pyrrol-1-yl)-N-(4-pyridinyl)-carbamic acid ethyl ester (6 g), in 50 ml of ethanol and 10 ml of 10% aqueous sodium hydroxide was warmed on a steam bath for thirty minutes, and thereafter cooled, diluted with water and extracted with dichloromethane. The organic extract was dried over anhydrous magnesium sulfate, filtered and evaporated to 5 g of oil. This oil was purified by HPLC (silica, ethyl acetate) to give 4 g of oil. This oil was converted to the maleate salt and twice recrystallized from isopropanol to give 1.7 g of crystals, mp 165°–166°.

Analysis:

Calculated for $C_{10}H_9N_3O \cdot C_4H_4O_4$: 55.44%C, 4.32%H, 13.86%N,

Found: 55.65%C, 4.49%H, 13.99%N.

EXAMPLE 42

4-[N-(1H-Pyrrol-1-yl)amino]-3-pyridinamine hydrochloride

In a Parr shaker apparatus was placed a mixture prepared from 6.0 g of 3-nitro-N-(1H-pyrrol-1-yl)-4-pyridinamine, 280 mg of 10% palladium on carbon, 50 ml of ethyl acetate and 150 ml of isopropanol. This was pressurized to 50 psi (pounds per square inch) with hydrogen and shaken for 8 hours at ambient temperature. The catalyst was then filtered and the solution was concentrated to an oil.

The amine was purified via HPLC (8% methanol/dichloromethane) to yield 3.4 g of an oil. This was converted to the hydrochloric acid salt in diethyl ether to yield 3.55 g of a solid, mp 200°–210° C. d. This was recrystallized from isopropanol/diethyl ether to give 2.25 g of a solid, mp 207°–209° C. decomp.

Analysis:

Calculated for $C_9H_{10}N_4 \cdot HCl$: 51.31%C, 5.26%H, 26.59%N,

Found: 51.51%C, 5.42%H, 26.29%N.

EXAMPLE 43

4-[N-Methyl-N-(1H-pyrrol-1-yl)amino]-3-pyridinamine

In a Parr shaker apparatus was placed a mixture prepared from 5.0 g of N-methyl-N-(1H-pyrrol-1-yl)-3-nitro-4-pyridinamine, 310 mg of 10% palladium on carbon, 175 ml of isopropanol and 30 ml of methanol This was shaken for 18 hours at ambient temperature.

The catalyst was filtered and the solution was concentrated to give 4.3 g of a solid, mp 100°–106° C. A 2.6 g portion of this material was sublimed under high vacuum at an oil bath temperature of 109° C. to give 2.1 g of crystals, mp 108°–111° C.

Analysis:

Calculated for $C_{10}H_{12}N_4$: 63.81%C, 6.43%H, 29.77%N,

Found: 63.67%C, 6.34%H, 29.80%N.

EXAMPLE 44

N-[3-[4-[N-Methyl-N-(1H-pyrrol-1-yl)amino]]-pyridinyl]-formamide

A solution of 4-[[N-methyl-N-(1H-pyrrol-1yl)-]amino]-3-pyridinamine (6.9g) in 25 ml of phenyl formate was stirred at ambient temperature for 40 hours.

The reaction mixture was added to 10% aqueous hydrochloric acid solution and this was washed with diethyl ether (2X). The aqueous phase was basified with aqueous sodium hydroxide and extracted with ethyl acetate (3X). The combined organics were dried (saturated sodium chloride solution, anhydrous magnesium sulfate) and concentrated to an oil.

The amide was purified via flash chromatography 4% methanol/dichloromethane) to yield 5.3 g of a solid, m.p. 119°–125° C. A portion of this solid was recrystallized from isopropyl ether:methanol (10:1) to give an analytically pure solid, m.p. 122°–125° C.

Analysis:

Calculated for $C_{11}H_{12}N_4O$: 61.10%C, 5.59%H, 25.91%N,

Found: 60.88%C, 5.59%H, 26.21%N.

EXAMPLE 45

2-Butyl-N-methyl-N-(1H-pyrrol-1-yl)-4-pyridinamine maleate

To a solution of N-methyl-N-(1H-pyrrol-1-yl)-4-pyridinamine (4.2 g) in 50 ml of anhydrous tetrahydrofuran cooled to −78° under nitrogen, was slowly dropped n-butyllithium (2.1 M in hexane, 13.8 ml). After the addition, the mixture was slowly warmed to ambient temperature. After stirring thirty minutes at ambient temperature, the reaction mixture was stirred with 300 ml of water and extracted with ethyl acetate. The organic extract was washed with water and saturated sodium chloride, dried over anhydrous magnesium sulfate, filtered and evaporated to 8.2 g of an oil. This oil was purified by HPLC (silica, 50% ethyl acetate-dichloromethane) to give 3.7 g of an oil. This oil was dissolved in 25 ml of warm isopropanol, and filtered, and a solution of maleic acid (1.9 g) in isopropanol was added. The crystals which formed upon cooling were collected and dried to give 5 g of crystals, mp 98°–100° C.

Analysis:

Calculated for $C_{14}H_{19}H_3 \cdot C_4H_4O_4$: 62.59%C, 6.71%H, 12.17%N,

Found: 62.22%C, 6.81%H, 11.90%N.

EXAMPLE 46

N-(4-Nitrophenyl)-N-(1H-pyrrol-1-yl)-4-pyridinamine hydrochloride

A solution of N-(1H-pyrrol-1-yl)-4-pyridinamine (4 g) in 25 ml of dimethylformamide was slowly added to an ice-cooled stirred suspension containing 1.2 g of sodium hydride in 10 ml of dimethylformamide. After the anion formation, a solution of 1-fluoro-4-nitrobenzene (4.2 g) in 10 ml of dimethylformamide was slowly added. After thirty minutes, the reaction mixture was stirred with ice water and extracted with ethyl acetate. The organic extract was washed with water and saturated sodium chloride solution and thereafter dried over anhydrous magnesium sulfate, filtered and evaporated to 10 g of an oil. This material was purified by flash chromatography (silica, 10% ethyl acetate in dichloromethane) to give 5.5 g of a solid, mp 98°–99° C. This material was converted to the hydrochloride salt in isopropanol to give 5.4 g of crystals, d 269°–270° C.

Analysis:
Calculated for $C_{15}H_{12}N_4O_2 \cdot HCl$: 56.88%C, 4.14%H, 17.69%N,
Found: 57.09%C, 4.35%H, 17.69%N.

EXAMPLE 47

1-[N-Methyl-N-(4-pyridinyl)amino]-1H-pyrrole-2-methanol

To a solution of 1-[N-methyl-N-(4-pyridinyl)]aminopyrrole-2-carboxaldehyde (8 g) in 100 ml of 2-propanol was added sodium borohydride (3 g) as a powder. After stirring two hours at ambient temperature the reaction mixture was stirred with 500 ml of water and extracted with ethyl acetate-ether. The organic extract was washed with water and saturated sodium chloride solution and thereafter dried over anhydrous magnesium sulfate, filtered and evaporated to 7.6 g of an oil. This oil was purified by high-pressure liquid chromatography (silica, 5% methanol in ethyl acetate) to give 6.2 g of a solid, mp 145°–148° C. A four gram portion was recrystallized from 2-propanol/petroleum ether to give 2.3 g of crystals, mp 150°–151° C.

Analysis:
Calculated for $C_{11}H_{13}N_3O$: 65.00%C, 6.45%H, 20.68%N,
Found: 64.92%C, 6.51%H, 20.73%N.

EXAMPLE 48

N-(2-Methoxymethyl-1H-pyrrol-1-yl)-N-methyl-4-pyridinamine oxalate

A solution of 1-[[N-methyl-N-(4-pyridinyl)]amino]-1H-pyrrole-2-methanol (3.5 g) in 20 ml of dimethylformamide was added to a stirred suspension containing 0.8 g of sodium hydride in 5 ml of dimethylformamide. After the anion formation the reaction mixture was cooled with ice and a solution of dimethyl sulfate (2.5 g) in 5 ml of dimethylformamide was slowly added. After one hour the reaction mixture was stirred with ice water and extracted with ethyl acetate. The organic extract was washed with water and saturated sodium chloride solution, and thereafter dried over anhydrous magnesium sulfate, filtered and evaporated to 6 g of an oil. This oil was purified by flash chromatography (silica, 5% methanol in ethyl acetate) to give 3.2 g of an oil. This oil was distilled via Kugelrohr to give 2.5 g of an oil, b.p. 150°–160° C. @0.01 mm. This oil was converted to the oxalate salt in 25 ml of warm 2-propanol to give upon cooling 3.4 g of crystals, d 157°–158° C.

Analysis:
Calculated for $C_{12}H_{15}N_3O \cdot C_2H_2O_4$: 54.71%C, 5.58%H, 13.68%N,
Found: 54.45%C, 5.58%H, 13.53%N.

EXAMPLE 49

N-(2-Ethenyl-1H-pyrrol-1-yl)-N-methyl-4-pyridinamine maleate

To n-butyllithium (2.1 M in hexane, 25 ml), diluted with 50 ml of anhydrous ether, cooled with an ice bath, was slowly added methyltriphenylphosphonium bromide (18 g) as a powder. To the freshly prepared methylenetriphenylphosphorane was added a solution of 1-[N-methyl-N-(4-pyridinyl)]aminopyrrole-2-carboxaldehyde (8 g) in 100 ml of anhydrous ether. After stirring cold for one hour, the reaction mixture was stirred with water and separated, and the aqueous phase was extracted with dichloromethane. The organic extract was washed with water and saturated sodium chloride solution, dried over anhydrous magnesium sulfate, filtered and evaporated to 26 g of oil. This oil was purified by HPLC (silica, ethyl acetate) to give 5.4 g of the product as an oil. This oil was converted to the maleate salt and recrystallized twice from isopropanol-ether to give 2.7 g of crystals, mp 87°–88°.

Analysis:
Calculated for $C_{12}H_{13}N_3 \cdot C_4H_4O_4$: 60.94%C, 5.43%H, 13.33%N,
Found: 60.70%C, 5.67%H, 13.22%N.

EXAMPLE 50

N-[2-(1-Propenyl)-1H-pyrrol-1-yl]-N-methyl-4-pyridinamine oxalate

To an ice-cooled suspension of ethyltriphenylphosphonium bromide (17 g) in 20 ml of anhydrous ether was slowly added n-butyllithium (2.1 M in hexane, 25 ml). To the freshly prepared ethylidenetriphenylphosphorane was added 1-[N-methyl-N-(4-pyridinyl)]aminopyrrole-2-carboxaldehyde (6 g) in 100 ml of ether and 25 ml of tetrahydrofuran. After one hour the reaction mixture was stirred with water and separated, and the aqueous phase was extracted with dichloromethane. The organic extracts were washed with water and saturated sodium chloride solution, dried over anhydrous magnesium sulfate, filtered and evaporated to 21 g of oil. This oil was purified by HPLC (silica, ethyl acetate) to give 4 g of oil. This oil was purified by column chromatography (alumina, ether) to give 2.3 g of oil. This oil was converted to the oxalate salt and recrystallized from isopropanol-ether to give 2.2 g of crystals, mp 141°–142°.

Analysis:
Calculated for $C_{13}H_{15}N_3 \cdot C_2H_2O_4$: 59.39%C, 5.65%H, 13.86%N,
Found: 59.11%C, 5.60%H, 13.79%N.

EXAMPLE 51

N-[2-(2-Phenylethenyl)-1H-pyrrol-1-yl]-N-methyl-4-pyridinamine hydrochloride

To a suspension of benzyltriphenylphosphonium chloride (17.4 g) in 225 ml of anhydrous ether was added n-butyllithium (2.5 M in hexanes, 18 ml). After thirty minutes a solution of 1-[N-methyl-N-(4-pyridinyl)]aminopyrrole-2-carboxaldehyde (6 g) in 200 ml of ether was added. After 1.5 hours, the mixture was stirred with ice-water and extracted with ether. The organic extract was washed with water and saturated sodium chloride solution, dried over anhydrous magnesium sulfate, filtered and evaporated to 20 g of oil. This was purified by flash chromatography (silica, 20% ethyl acetate in dichloromethane) to give 12 g of oil. This oil was converted to the hydrochloride salt and recrystallized from ethanol-ether to give 6.4 g of crystals, d 241°–243°. A 3 g sample was recrystallized from ethanol-ether to give 2.7 g of crystals, d 244°–245°.

Analysis:
Calculated for $C_{18}H_{17}N_3.HCl$: 69.33%C, 5.82%H, 13.48%N,
Found: 69.25%C, 5.65%H, 13.82%N.

EXAMPLE 52

N-[2-(2-Methoxyethenyl)-1H-pyrrol-1-yl]-N-methyl-4-pyridinamine maleate

To a suspension of (methoxymethyl)triphenylphosphonium chloride (90% technical grade, 25 g) in 200 ml of anhydrous tetrahydrofuran, cooled with an ice bath, was slowly added n-butyllithium (2.1 M) in hexane, 34 ml). To the freshly prepared methoxymethylenetriphenylphosphorane was added a solution of 1-[N-methyl-N-(4-pyridinyl)]aminopyrrole-2-carboxaldehyde (6 g) in 50 ml of tetrahydrofuran. After thirty minutes, the reaction mixture was stirred with 500 ml of ice-water. After separation, the aqueous phase was extracted with dichloromethane and the combined organics were washed with water and saturated sodium chloride solution, dried over anhydrous magnesium sulfate, filtered and evaporated to 28 g of oil. This oil was purified by HPLC (silica, ethyl acetate) to give 6 g of oil. This oil was purified by column chromatography (alumina, dichloromethane) to give 5 g of oil. This oil was converted to the maleate salt and recrystallized twice from isopropanol-ether to give 2.4 g of crystals, mp 125°–126°.

Analysis
Calculated for $C_{13}H_{15}N_3O . C_4H_4O_4$: 59.12%C, 5.55%H, . 12.17%N,
Found: 58.89%C, 5.58%H, 12.06%N.

EXAMPLE 53

N-(2-Ethyl-1H-pyrrol-1-yl)-N-methyl-4-pyridinamine hydrochloride

A solution of N-(2-ethenyl-1H-pyrrol-1-yl)-N-methyl-4-pyridinamine (5.2 g) in 250 ml of ethanol containing 350 mg of platinum oxide was hydrogenated at 50 psi (pounds per square inch) for three hours and thereafter the product was filtered and evaporated to 5 g of oil. This oil was purified by flash chromatography (silica, 25% dichloromethane in ethyl acetate) to give 3.9 g of oil. This oil was converted to the hydrochloride salt and recrystallized twice from isopropanol-ether to give 3.0 g of crystals, mp 197°–198°.

Analysis:
Calculated for $C_{12}H_{15}N_3.HCl$: 60.62%C, 6.78%H, 17.68%N,
Found: 60.32%C, 6.77%H, 17.54%N.

EXAMPLE 54

N-Methyl-N-(2-propyl-1H-pyrrol-1-yl)-4-pyridinamine hydrochloride

A solution of N-[2-(1-propenyl)-1H-pyrrol-1-yl]-N-methyl-4-pyridinamine (7 g) in 250 ml of ethanol containing 350 mg of platinum oxide was hydrogenated at 50 psi for two days, and thereafter the product was filtered and evaporated to 9 g of oil. This oil was purified by flash chromatography (silica, ethyl acetate) to give 8 g of oil. This oil was purified by column chromatography (alumina, ether) to give 5 g of oil. This oil was converted to the hydrochloride salt and recrystallized from isopropanol-ether and from ethanol-ether to give 2.8 g of crystals, mp 210°–212°.

Analysis
Calculated for $C_{13}H_{17}N_3.HCl$: 62.02%C, 7.21%H, 16.69%N,
Found: 61.92%C, 7.24%H, 16.64%N.

EXAMPLE 55

N-Methyl-N-(2-phenylethyl-1H-pyrrol-1-yl)-4-pyridinamine hydrochloride

A solution of N-[2-(2-phenylethenyl)-1H-pyrrol-1-yl]-N-methyl-4-pyridinamine (3 g) in 250 ml of ethanol containing 350 mg of platinum oxide was hydrogenated at 50 psi for twenty-four hours and therefter the product was filtered and evaporated to 4 g of oil. This oil was purified by flash chromatography (silica, ethyl acetate) to give 3 g of oil. This oil was converted to the hydrochloride salt and recrystallized twice from ethanol-ether to give 2.1 g of crystals, mp 173°–174°.

Analysis:
Calculated for $C_{18}H_{19}N_3.HCl$: 68.89%C, 6.42%H, 13.39%N,
Found: 69.15%C, 6.33%H, 13.52%N.

EXAMPLE 56

4-Nitro-N-(1H-pyrrol-1-yl)-3-pyridinamine-N-oxide

A solution of 5 g of 3-fluoro-4-nitropyridine-N-oxide (disclosed in Talik and Talik, Roczniki Chemii, 38, 777 (1964)) and 5 g of 1-aminopyrrole in 75 ml of ethanol was stirred one hour at 85° and thereafter cooled and filtered to give 6 g of 4-nitro-N-(1H-pyrrol-1-yl)-3-pyridinamine-N-oxide as a solid, d 224°–226°. A 3 g sample was recrystallized from ethanol to give 2.2 g of crystals, d 224°–226°.

Analysis:
Calculated for $C_9H_8N_4O_3$: 49.09%C, 3.66%H, 25.45%N,
Found: 49.16%C, 3.68%H, 25.60%N.

EXAMPLE 57

N-Methyl-N-(1H-pyrrol-1-yl)-4-nitro-3-pyridinamine-N-oxide

A solution of 4-nitro-N-(1H-pyrrol-1-yl)-3-pyridinamine-N-oxide (3.9 g) in 50 ml of dimethylformamide was added to a cooled suspension of sodium hydride (60% oil dispersion, 0.8 g, washed with hexanes) in 5 ml of dimethylformamide. After the anion formation, a solution of dimethyl sulfate (2.7 g) in 5 ml of dimethylformamide was added. After stirring twenty hours at ambient temperature, the reaction mixture was stirred with water and extracted with dichloromethane. The organic extract was washed with water and saturated sodium chloride solution, dried over anhydrous magnesium sulfate, filtered and evaporated to 4.5 g of oil. This oil was purified by flash chromatography (silica, 10% ethyl acetate in dichloromethane) to give 4 g of solid, mp 135°–140°. This material was purified by HPLC (silica, 20% ethyl acetate in dichloromethane) to give 3.5 g of solid, mp 140°–144°. This material was recrystallized from absolute ethanol to give 2.1 g of needles, mp 150°–151°.

Analysis:

Calculated for $C_{10}H_{10}N_4O_3$: 51.28%C, 4.30%H, 23.93%N,

Found: 51.25%C, <4.37%H, 23.94%.

EXAMPLE 58

3-[N-Methyl-N-(1H-pyrrol-1-yl)]-3,4-pyridinediamine hydrochloride

A solution of N-methyl-N-(1H-pyrrol-1-yl)-4-nitro-3-pyridinamine-N-oxide (6 g) in 500 ml of absolute ethanol containing 0.5 g of platinum oxide was hydrogenated at 50 psi for six hours and thereafter the product was filtered and evaporated to 5 g of oil. This oil was purified by flash chromatography (silica, 10% methanol in dichloromethane) to give 3.6 g of oil. This oil was converted to the hydrochloride salt and recrystallized twice from ethanol-ether to give 2.9 g of crystals, d 258°–260°.

Analysis:

Calculated for $C_{10}H_{12}N_4 \cdot HCl$: 53.45%C, 5.83%H, 24.94%N,

Found: 53.21%C, 6.00%H, 24.65%N.

EXAMPLE 59

N-(2-Cyano-1H-pyrrol-1-yl)-N-methyl-4-pyridinamine hydrochloride

To a solution of 1-[N-methyl-N-(4-pyridinyl)-]aminopyrrole-2-carboxaldehyde (9.5 g) in 50 ml of pyridine was added hydroxylamine hydrochloride (10 g). After stirring one hour at ambient temperature, the reaction mixture was evaporated, stirred with water and extracted with ether. The organic extract was washed with water and saturated sodium chloride solution, dried over anhydrous magnesium sulfate, filtered and evaporated to 13 g of oil. This oil was purified by HPLC to give a total of 9.2 g of isomeric oximes. The NMR (DMSO-$d_6$) and mass spectra (M$^+$=216) supported the conversion to the oxime intermediate.

To 4.3 g of the oxime in 50 ml of ether were successively added pyridine (2 g) and benzenesulfonyl chloride (4.2 g). The reaction mixture was warmed on a steam bath to dryness (30 minutes) and thereafter cooled, stirred with water, basified with sodium carbonate and extracted with ethyl acetate. The organic extract was washed with water and saturated sodium chloride solution, dried over anhydrous magnesium sulfate, filtered and evaporated to 4 g of waxy residue. This material was purified by HPLC (silica, ethyl acetate) to give 3.2 g of solid, mp 88°–90°. This material was converted to the hydrochloride salt in 25 ml of warm isopropanol to give upon cooling 3.3 g of crystals, mp 251°–252°.

Analysis:

Calculated for $C_{11}H_{10}N_4 \cdot HCl$: 56.29%C, 4.72%H, 23.88%N,

Found: 56.19%C, 4.98%H, 23.73%N.

We claim:

1. A compound of the formula

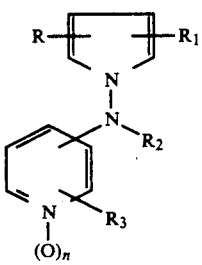

where n is 0 or 1; R is hydrogen or loweralkyl; $R_1$ is hydrogen, loweralkyl, halogen, cyano, loweralkanoyl, arylloweralkanoyl, aroyl, —CH(OH)$R_4$, —C(OH)$R_4R_5$ or —CH$_2$OR$_5$, —CH=CR$_6R_7$, —CH=CHCN, —CH=CHOCH$_3$, —CH=CH-CO$_2$C$_2$H$_5$,

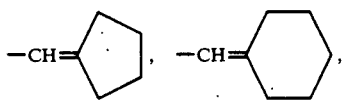

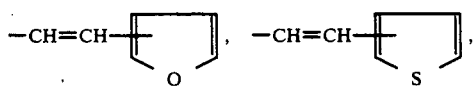

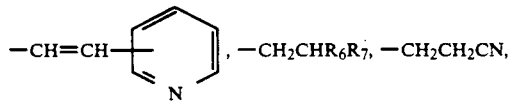

—CH$_2$CH$_2$OCH$_3$, —CH$_2$CH$_2$CO$_2$C$_2$H$_5$,

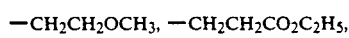

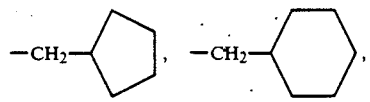

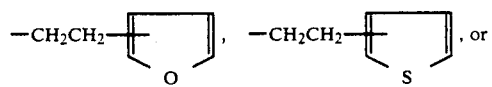

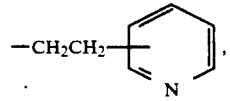

$R_4$ being hydrogen, loweralkyl, arylloweralkyl or aryl, $R_5$ being loweralkyl, aryl or arylloweralkyl, $R_6$ being hydrogen or loweralkyl and $R_7$ being hydrogen, loweralkyl or aryl; $R_2$ is hydrogen, loweralkyl, loweralkenyl, loweralkynyl, —CH$_2$CO$_2$C$_2$H$_5$, arylloweralkyl, phenyl, nitrophenyl, cyanophenyl, trifluoromethylphenyl, aminophenyl, loweralkanoylaminophenyl, loweralkoxycarbonyl, arylloweralkoxycarbonyl, aryloxycarbonyl, loweralkylaminocarbonyl, arylloweralkylaminocarbonyl, arylaminocarbonyl, alkanoyl, arylloweralkanoyl, aroyl, alkenoyl, alkynoyl, —CH$_2$C≡CCH$_2$—NR'R", —CH$_2$CH=CHCH$_2$—NR'R" or —CH$_2$CH$_2$CH$_2$CH$_2$—NR'R", R' and R" being independently loweralkyl or —NR'R" taken as a hole being

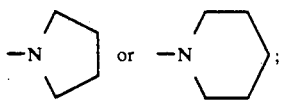

and R₃ is hydrogen, NO₂, NH₂, halogen, loweralkanoylamino, arylloweralkanoylamino, aroylamino or loweralkyl; the term aryl in each occurrence signifying a phenyl group having 0, 1, 2, or 3 substituents each of which being independently loweralkyl, loweralkoxy, halogen, CF₃, NO₂ or CN; with the proviso that when n is 0, R₂ is phenyl, R₃ is hydrogen and the pyridine moiety is 2-pyridinyl, R and R₁ may not be 2-methyl and 5-methyl; or pharmaceutically acceptable acid addition salts thereof.

2. The compound as defined in claim 1 where R₃ is H.

3. The compound as defined in claim 1 where R₂ is H, loweralkyl, loweralkenyl, loweralkynyl, arylloweralkyl or —CH₂C≡CCH₂—NR'R''.

4. The compound as defined in claim 1 where R₁ is H, loweralkyl, halogen, loweralkanoyl, —CH(OH)R₄, —CH=CR₆R₇ or —CH=CHOCH₃, where R₄ is H or loweralkyl, R₆ is H or loweralkyl and R₇ is H, loweralkyl or aryl.

5. The compound as defined in claim 2 where R₂ is H, loweralkyl, loweralkenyl, loweralkynyl, arylloweralkyl or —CH₂C≡CCH₂—NR'R'', and R₁ is H, loweralkyl, halogen, loweralkanoyl, —CH(OH)R₄, —CH=CR₆R₇ or —CH=CHOCH₃, where R₄ is H or loweralkyl, R₆ is H or loweralkyl and R₇ is H, loweralkyl or aryl.

6. The compound as defined in claim 1, where the pyridine ring is connected to the amino nitrogen via the 4-position.

7. The compound as defined in claim 3, where the pyridine ring is connected to the amino nitrogen via the 4-position.

8. The compound as defined in claim 4, where the pyridine ring is connected to the amino nitrogen via the 4-position.

9. The compound as defined in claim 5, where the pyridine ring is connected to the amino nitrogen via the 4-position.

10. The compound as defined in claim 1, which is N-(butyl)-N-(1H-pyrrol-1-yl)-4-pyridinamine.

11. The compound as defined in claim 1, which is N-(2-propenyl)-N-(1H-pyrrol-1-yl)-4-pyridinamine.

12. The compound as defined in claim 1, which is N-(2-propynyl)-N-(1H-pyrrol-1-yl)-4-pyridinamine.

13. The compound as defined in claim 1, which is N-[4-(pyrrolidin-1-yl)-2-butynyl]-N-(1H-pyrrol-1-yl)-4-pyridinamine.

14. The compound as defined in claim 1, which is N-(2-chloro-1H-pyrrol-1-yl)-N-propyl-4-pyridinamine.

15. The compound as defined in claim 1, which is N-(2-ethenyl-1H-pyrrol-1-yl)-N-methyl-4-pyridinamine.

16. The compound as defined in claim 1, which is N-[2-(1-propenyl)-1H-pyrrol-1-yl]-N-methyl-4-pyridinamine.

17. The compound as defined in claim 1, which is N-[2-(2-phenylethenyl)-1H-pyrrol-1-yl]-N-methyl-4-pyridinamine.

18. The compound as defined in claim 1, which is N-[2-(2-methoxyethenyl)-1H-pyrrol-1-yl]-N-methyl-4-pyridinamine.

19. The compound as defined in claim 1, which is N-(2-ethyl-1H-pyrrol-1-yl)-N-methyl-4-pyridinamine.

20. The compound as defined in claim 1, which is N-(methyl-N-(2-propyl-1H-pyrrol-1-yl)-4-pyridinamine.

21. The compound as defined in claim 1, which is N-methyl-N-(2-phenylethyl-1H-pyrrol-1-yl)-4-pyridinamine.

22. The compound as defined in claim 1, which is 4-nitro-N-(1H-pyrrol-1-yl)-3-pyridinamine-N-oxide.

23. The compound as defined in claim 1, which is N-methyl-N-(1H-pyrrol-1-yl)-4-nitro-3-pyridinamine-N-oxide.

24. The compound as defined in claim 1, which is 3-[N-methyl-N-(1H-pyrrol-1-yl)9 -3,4-pyridinediamine.

25. The compound as defined in claim 1, which is N-(2-cyano-1H-pyrrol-1-yl)-N-methyl-4-pyridinamine.

26. The compound as defined in claim 1, which is N-methyl-N-(2-methyl-1H-pyrrol-1-yl)-4-pyridinamine.

27. The compound as defined in claim 1, which is N-propyl-N-(2-methyl-1H-pyrrol-1-yl)-4-pyridinamine.

28. The compound as defined in claim 1, which is N-methyl-N-(2,5-dimethyl-1H-pyrrol-1-yl)-4-pyridinamine;

29. The compound as defined in claim 1, which is N-methyl-N-[2-[2-(2-methylphenyl)ethenyl]-1H-pyrrol-1-yl]-4-pyridinamine.

30. The compound as defined in claim 1, which is N-ethyl-N-[2-[2-(4-methylphenyl)ethenyl]-1H-pyrrol-1-yl]-4-pyridinamine.

31. The compound as defined in claim 1, which is N-methyl-N-[2-[2-(2-methoxyphenyl)ethenyl]-1H-pyrrol-1-yl]-4-pyridinamine.

32. The compound as defined in claim 1, which is N-propyl-N-[2-[2-(3-methoxyphenyl)ethenyl]-1H-pyrrol-1-yl]-4-pyridinamine.

33. The compound as defined in claim 1, which is N-methyl-N-[2-[2-(4-methoxyphenyl)ethenyl]-1H-pyrrol-1]-4-pyridinamine.

34. The compound as defined in claim 1, which is N-methyl-N-[2-[2-(2-chlorophenyl)ethenyl]-1H-pyrrol-1-yl]-4-pyridinamine.

35. The compound as defined in claim 1, which is N-methyl-N-[2-[2-(4-chlorophenyl)ethenyl]-1H-pyrrol-1-yl]-4-pyridinamine.

36. The compound as defined in claim 1, which is N-methyl-N-[2-[2-(2-methylphenyl)ethyl]-1H-pyrrol-1-yl]-4-pyridinamine.

37. The compound as defined in claim 1, which is N-ethyl-N-[2-[2-(3-methylphenyl)ethyl]-1H-pyrrol-1-yl]-4-pyridinamine.

38. The compound as defined in claim 1, which is N-propyl-N-[2-[2-(3-methoxyphenyl)ethyl]-1H-pyrrol-1-yl]-4-pyridinamine.

39. The compound as defined in claim 1, which is N-methyl-N-[2-[2-(4-methoxyphenyl)ethyl]-1H-pyrrol-1-yl]-4-pyridinamine.

40. The compound as defined in claim 1, which is N-ethyl-N-[2-[2-(2-chlorophenyl)ethyl]-1H-pyrrol-1-yl]-4-pyridinamine.

41. The compound as defined in claim 1, which is N-methyl-N-[2-[2-(4-methoxyphenyl)ethyl]-1H-pyrrol-1-yl]-4-pyridinamine.

42. The compound as defined in claim 1, which is N-(1H-pyrrol-1-yl)-3-pyridinamine.

43. The compound as defined in claim 1, which is N-methyl-N-(1H-pyrrol-1-yl)-3-pyridinamine.

44. A pharmaceutical composition which comprises an effective memory enhancing amount of a compound as defined in claim 1 in admixture with an inert carrier.

45. A method of treating a patient in need of memory enhancement which comprises administering to the patient an effective memory enhancing amount of a compound as defined in claim 1.

* * * * *